United States Patent
Jansson et al.

(10) Patent No.: US 9,220,624 B2
(45) Date of Patent: Dec. 29, 2015

(54) POSTERIOR CRUCIATE LIGAMENT SUPPORT BRACE

(75) Inventors: Kyle Jansson, Monona, WI (US); Robert Francis LaPrade, Chanhassen, MN (US)

(73) Assignee: OSSUR HF, Reykjavik (IS)

( * ) Notice: Subject to any disclaimer, the term of this patent is extended or adjusted under 35 U.S.C. 154(b) by 198 days.

(21) Appl. No.: 13/232,854

(22) Filed: Sep. 14, 2011

(65) Prior Publication Data

US 2012/0071803 A1 Mar. 22, 2012

Related U.S. Application Data

(60) Provisional application No. 61/383,432, filed on Sep. 16, 2010.

(51) Int. Cl.
*A61F 5/37* (2006.01)
*A61F 13/00* (2006.01)
*A61B 19/00* (2006.01)
*A63B 21/22* (2006.01)
*A63B 21/015* (2006.01)
(Continued)

(52) U.S. Cl.
CPC ................ *A61F 5/0125* (2013.01); *A61F 5/00* (2013.01); *A61F 5/01* (2013.01); *A61F 5/0102* (2013.01); *A61F 5/0123* (2013.01); *A63B 21/00* (2013.01); *A63B 21/02* (2013.01); *A63B 21/04* (2013.01); *A63B 21/045* (2013.01); *A63B 21/0455* (2013.01); *A63B 21/055* (2013.01); *A61F 2005/0179* (2013.01)

(58) Field of Classification Search
CPC ........... A61F 5/00; A61F 5/01; A61F 5/0102; A61F 5/0123; A61F 5/0125; A61F 2005/0179; A63B 21/00; A63B 21/02; A63B 21/04; A63B 21/0455; A63B 21/055
USPC ............ 128/846, 869, 882; 602/5, 16, 23, 26, 602/60–62; 482/110, 115, 121, 129
See application file for complete search history.

(56) References Cited

U.S. PATENT DOCUMENTS

| 73,768 A | 1/1868 | Allen |
| 1,601,659 A | 9/1926 | Van Harlingen |

(Continued)

FOREIGN PATENT DOCUMENTS

| DE | 33 20 274 A1 | 12/1984 |
| DE | 19631632 A1 | 2/1998 |

(Continued)

OTHER PUBLICATIONS

Copenheaver, Blaine R., "International Search Report and Written Opinion re Application No. PCT/US11/051627", Jan. 6, 2012, Published in: US.

(Continued)

*Primary Examiner* — Alireza Nia
*Assistant Examiner* — Brandon L Jackson
(74) *Attorney, Agent, or Firm* — Workman Nydegger

(57) ABSTRACT

This disclosure describes systems, methods, and apparatus for a knee brace providing a dynamic resistance or anterior force to a shank of a leg in order to replicate PCL forces of a healthy PCL. A dynamic force dependent upon knee flexion angle provides faster and safer PCL injury healing since the dynamic force better replicates the forces that a healthy PCL would exert on the tibia and femur.

19 Claims, 14 Drawing Sheets

(51) Int. Cl.
  *A63B 21/02* (2006.01)
  *A63B 21/04* (2006.01)
  *A61F 5/00* (2006.01)
  *A61F 13/06* (2006.01)
  *A61F 5/01* (2006.01)
  *A63B 21/00* (2006.01)
  *A63B 21/045* (2006.01)
  *A63B 21/055* (2006.01)

(56) References Cited

U.S. PATENT DOCUMENTS

| | | |
|---|---|---|
| 2,195,024 A | 3/1940 | Bullock |
| 2,467,907 A | 4/1949 | Peckham |
| 2,536,454 A | 1/1951 | McIntyre |
| 2,558,986 A | 7/1951 | Seelert |
| 2,959,168 A | 11/1960 | Shook |
| 3,753,625 A | 8/1973 | Fabrizio et al. |
| 3,976,057 A | 8/1976 | Barclay |
| 4,064,569 A | 12/1977 | Campbell |
| 4,088,130 A | 5/1978 | Applegate |
| 4,100,918 A | 7/1978 | Glancy |
| 4,145,766 A | 3/1979 | May |
| 4,220,148 A | 9/1980 | Lehneis |
| 4,298,992 A | 11/1981 | Burstein et al. |
| 4,320,747 A | 3/1982 | Daniell, Jr. |
| 4,340,041 A | 7/1982 | Frank |
| 4,361,142 A | 11/1982 | Lewis et al. |
| 4,370,977 A | 2/1983 | Mauldin et al. |
| 4,372,298 A | 2/1983 | Lerman |
| 4,407,276 A | 10/1983 | Bledsoe |
| 4,428,369 A | 1/1984 | Peckham et al. |
| 4,433,679 A | 2/1984 | Mauldin et al. |
| 4,443,679 A | 4/1984 | Balordi |
| 4,463,751 A | 8/1984 | Bledsoe |
| 4,506,661 A | 3/1985 | Foster |
| 4,520,802 A | 6/1985 | Mercer et al. |
| 4,523,585 A | 6/1985 | Lamb et al. |
| 4,649,906 A | 3/1987 | Spademan |
| 4,655,201 A | 4/1987 | Pirmantgen |
| 4,691,694 A | 9/1987 | Boyd et al. |
| 4,697,583 A | 10/1987 | Mason et al. |
| 4,723,539 A | 2/1988 | Townsend |
| 4,732,143 A | 3/1988 | Kausek et al. |
| 4,733,656 A | 3/1988 | Marquette |
| 4,768,762 A | 9/1988 | Lund |
| 4,773,404 A | 9/1988 | Townsend |
| 4,790,299 A | 12/1988 | Marquette |
| 4,793,333 A | 12/1988 | Marquette |
| 4,817,588 A | 4/1989 | Bledsoe |
| 4,856,500 A | 8/1989 | Spadman |
| 4,856,501 A | 8/1989 | Castillo et al. |
| 4,865,024 A | 9/1989 | Hensley et al. |
| 4,890,607 A | 1/1990 | Townsend |
| 4,911,709 A | 3/1990 | Marlow et al. |
| 4,955,369 A | 9/1990 | Bledsoe et al. |
| 4,961,416 A | 10/1990 | Moore et al. |
| 4,966,133 A | 10/1990 | Kausek |
| 4,982,732 A | 1/1991 | Morris |
| 4,991,571 A | 2/1991 | Kausek |
| 5,002,045 A | 3/1991 | Spademan |
| 5,018,514 A | 5/1991 | Grood et al. |
| 5,020,797 A | 6/1991 | Burns |
| 5,038,765 A | 8/1991 | Young et al. |
| 5,052,375 A | 10/1991 | Stark et al. |
| 5,063,917 A | 11/1991 | Young et al. |
| 5,176,622 A | 1/1993 | Anderson et al. |
| 5,213,094 A | 5/1993 | Bonutti |
| 5,230,696 A | 7/1993 | Silver et al. |
| 5,230,697 A | 7/1993 | Castillo et al. |
| 5,261,871 A | 11/1993 | Greenfield |
| 5,347,894 A | 9/1994 | Fischer |
| 5,437,611 A | 8/1995 | Stern |
| 5,443,444 A | 8/1995 | Pruyssers |
| 5,456,268 A | 10/1995 | Bonutti |
| 5,472,410 A | 12/1995 | Hamersly |
| 5,472,412 A | 12/1995 | Knoth |
| 5,514,082 A | 5/1996 | Smith, III |
| 5,588,956 A | 12/1996 | Billotti |
| 5,599,288 A | 2/1997 | Shirley et al. |
| 5,628,722 A | 5/1997 | Solomonow et al. |
| 5,658,241 A | 8/1997 | Deharde et al. |
| 5,662,596 A | 9/1997 | Young |
| 5,685,830 A | 11/1997 | Bonutti |
| 5,807,294 A | 9/1998 | Cawley et al. |
| 5,857,988 A | 1/1999 | Shirley |
| 5,873,847 A | 2/1999 | Bennett et al. |
| 5,891,061 A | 4/1999 | Kaiser |
| 5,891,071 A | 4/1999 | Stearns et al. |
| 5,954,677 A | 9/1999 | Albrecht et al. |
| 5,997,493 A | 12/1999 | Young |
| 6,004,283 A | 12/1999 | Young |
| 6,074,355 A | 6/2000 | Bartlett |
| 6,110,137 A | 8/2000 | Bastyr et al. |
| 6,129,690 A | 10/2000 | Hamlin et al. |
| RE37,209 E | 6/2001 | Hensley et al. |
| RE37,297 E | 7/2001 | Smith, III |
| 6,331,169 B1 | 12/2001 | Bastyr et al. |
| 6,409,693 B1 | 6/2002 | Brannigan |
| 6,425,166 B1 | 7/2002 | Seligman et al. |
| 6,551,264 B1 | 4/2003 | Cawley et al. |
| 6,666,837 B2 | 12/2003 | Weihermuller |
| 6,740,054 B2 | 5/2004 | Stearns |
| 6,752,775 B2 | 6/2004 | Seligman et al. |
| 6,936,020 B2 | 8/2005 | Davis |
| 6,993,808 B1 | 2/2006 | Bennett et al. |
| 7,004,919 B2 | 2/2006 | Gaylord et al. |
| 7,097,627 B2 | 8/2006 | Enzerink et al. |
| 7,150,721 B2 | 12/2006 | Houser |
| 7,182,740 B1 | 2/2007 | Castillo |
| 7,192,407 B2 | 3/2007 | Seligman et al. |
| 7,201,728 B2 | 4/2007 | Sterling |
| 7,207,960 B2 | 4/2007 | Kenney |
| 7,235,058 B2 | 6/2007 | Doty et al. |
| 7,309,322 B2 | 12/2007 | Albrecht et al. |
| 7,311,687 B2 | 12/2007 | Hoffmeier et al. |
| 7,435,234 B2 | 10/2008 | Gamada |
| 7,500,957 B2 | 3/2009 | Bledsoe |
| 7,534,217 B2 | 5/2009 | Seligman et al. |
| 7,534,219 B2 | 5/2009 | Stearns |
| 7,544,174 B2 | 6/2009 | Nathanson |
| 7,553,289 B2 | 6/2009 | Cadichon |
| 7,662,122 B2 | 2/2010 | Sterling |
| 7,722,555 B2 | 5/2010 | Doty et al. |
| 7,806,842 B2 | 10/2010 | Stevenson et al. |
| 7,811,242 B2 | 10/2010 | Seligman |
| 7,846,115 B2 | 12/2010 | Seligman et al. |
| 7,850,632 B2 | 12/2010 | Gilmour |
| 7,927,299 B2 | 4/2011 | Krause |
| 7,963,933 B2 | 6/2011 | Nace |
| 8,048,013 B2 | 11/2011 | Ingimundarson et al. |
| 8,128,587 B2 | 3/2012 | Stevenson et al. |
| 2002/0013544 A1 | 1/2002 | Stearns |
| 2002/0052568 A1 | 5/2002 | Houser et al. |
| 2002/0133108 A1 | 9/2002 | Jagodzinski |
| 2004/0002674 A1 | 1/2004 | Sterling |
| 2004/0049140 A1 | 3/2004 | Doty et al. |
| 2004/0054307 A1 | 3/2004 | Mason et al. |
| 2004/0054311 A1 | 3/2004 | Sterling |
| 2004/0068215 A1 | 4/2004 | Adelson et al. |
| 2004/0097859 A1 | 5/2004 | Stearns |
| 2005/0015156 A1 | 1/2005 | Hikichi |
| 2005/0020951 A1 | 1/2005 | Gaylord et al. |
| 2005/0177082 A1 | 8/2005 | Bledsoe |
| 2005/0245853 A1 | 11/2005 | Scorvo |
| 2005/0273025 A1 | 12/2005 | Houser |
| 2006/0100560 A1 | 5/2006 | Gilmour |
| 2006/0100561 A1 | 5/2006 | Gilmour |
| 2006/0116616 A1 | 6/2006 | Albrecht et al. |
| 2006/0135902 A1 | 6/2006 | Ingimundarson et al. |
| 2006/0142680 A1 | 6/2006 | Iarocci |
| 2007/0010772 A1 | 1/2007 | Ryan |
| 2007/0100265 A1 | 5/2007 | Gamada |
| 2007/0232972 A1 | 10/2007 | Martinez |

(56) References Cited

U.S. PATENT DOCUMENTS

| | | | |
|---|---|---|---|
| 2007/0270976 | A1 | 11/2007 | DeHarde et al. |
| 2008/0051684 | A1 | 2/2008 | Gamada |
| 2008/0249448 | A1 | 10/2008 | Stevenson et al. |
| 2008/0294079 | A1 | 11/2008 | Sterling et al. |
| 2009/0105622 | A1 | 4/2009 | Sterling et al. |
| 2009/0124948 | A1 | 5/2009 | Ingimundarson et al. |
| 2009/0171469 | A1* | 7/2009 | Thorsteinsson et al. ........ 623/26 |
| 2009/0287128 | A1 | 11/2009 | Ingimundarson et al. |
| 2010/0056970 | A1 | 3/2010 | Nace |
| 2011/0098618 | A1 | 4/2011 | Fleming |
| 2012/0046585 | A1 | 2/2012 | Lee et al. |
| 2012/0059296 | A1 | 3/2012 | Kompa |
| 2012/0157902 | A1 | 6/2012 | Castillo et al. |
| 2013/0110020 | A1 | 5/2013 | Ingimundarson et al. |
| 2013/0331754 | A1 | 12/2013 | Dunn et al. |

FOREIGN PATENT DOCUMENTS

| | | |
|---|---|---|
| DE | 19645076 A1 | 5/1998 |
| DE | 198 11 925 A1 | 10/1999 |
| DE | 10259751 A1 | 7/2004 |
| DE | 10 2010 006 089 A1 | 8/2010 |
| EP | 0841044 A1 | 5/1998 |
| EP | 0941722 A1 | 9/1999 |
| EP | 1114619 A1 | 7/2001 |
| EP | 1 302 184 A1 | 4/2003 |
| EP | 1575464 A1 | 9/2005 |
| EP | 1 880 802 A2 | 1/2008 |
| EP | 2 612 624 A1 | 7/2013 |
| FR | 2 122 846 A5 | 9/1972 |
| FR | 2 486 852 A1 | 1/1982 |
| FR | 2 663 380 A1 | 12/1991 |
| FR | 2 723 842 A1 | 3/1996 |
| FR | 2 777 489 A1 | 10/1999 |
| FR | 2828093 A1 | 2/2003 |
| GB | 1 213 855 A | 11/1970 |
| WO | 8604228 A1 | 7/1986 |
| WO | 95/27451 A1 | 10/1995 |
| WO | 9616615 A1 | 6/1996 |
| WO | 2004056293 A1 | 7/2004 |
| WO | 2006/044423 A2 | 4/2006 |
| WO | 2010087899 A2 | 8/2010 |

OTHER PUBLICATIONS

Bledsoe Axiom/Axiom-D Custom 7 OTS Knee Brace, "Application Instructions & Patient Manual", http://www.bledsoebrace.com/pdf/Al/Axiom-Al.pdf, Jan. 2007, pp. 1-4, vol. CP020223, Rev B, Publisher: Bledsoe Brace Systems, Published in: US.

Breg 360 Customer Care, "Fusion OA", Product page http://www.breg.com/knee-bracing/oa/fusion-oa.html downloaded, Oct. 2011, Publisher: Orthofix, Published in: US.

Breg 360 Customer Care, "Fusion XT OA", Product page http://www.breg.com/knee-bracing/oa/fusion-xt-oa.html downloaded, Oct. 2011, Publisher: Orthofix, Published in: US.

Breg 360 Customer Care, "X2K-OA", Product page http://www.breg.com/knee-bracing/oa/x2k-oa.html downloaded, Oct. 2011, Publisher: Orthofix, Published in: US.

Defrate, L.E., et al., "In Vivo Function of the Posterior Cruciate Ligament During Weightbearing Knee Flexion", "Am J Sports Med", Dec. 2004, pp. 1923-1928, vol. 32, No. 8, Publisher: American Orthopaedic Society for Sports Medicine, Published in: US.

Donjoy, "Armor Fourcepoint", Product pages http://www.donjoy.com/armorfp/ downloaded, Oct. 2011, p. 2 Published in: US.

Markolf, K.L., "Changes in Knee Laxity and Ligament Force After Sectioning the Posteromedial Bundle of the Posterior Cruciate Ligament", "Arthroscopy: The Journal of Arthroscopic and Related Surgery", Oct. 2006, pp. 1100-1106, vol. 22, No. 10, Publisher: Arthroscopy Association of North America, Published in: US.

Ossur, "CTi Custom", Product page from http:www.ossur.com/?PageID=13230 downloaded, Oct. 2011, Publisher: Ossur Americas, Published in: US.

Papannagari, R., et al., "Function of Posterior Cruciate Ligament Bundles During In Vivo Knee Flexion", "Am J Sports Med", Sep. 2007, pp. 1507-1512, vol. 35, No. 9, Publisher: American Orthopaedic Society for Sports Medicine, Published in: US.

Cascade, "Jack PCL Brace", http://www.cascade-usa.com/customer/caorsu/images/PDF/SSN_jackPCL.pdf downloaded, Oct. 2004, Publisher: Cascade Orthopedic Supply, Inc., Published in: US.

Cussac, Yolaine, "International Preliminary Report on Patentability re Application No. PCT/US2011/051627", Mar. 28, 2013, p. 10 Published in: CH.

Knapik, Joseph J. et al., Isometric, Isotonic and Isokinetic Torque Variations in Four Muscle Groups Through a Range of Joint Motion, "Physical Therapy: Journal of the American Physical Therapy Association and de Fysiotherapeut", vol. 63, No. 6, pp. 938-947, downloaded from http://ptjournal.apta.org/ on Apr. 15, 2014.

International Search Report from corresponding PCT Application No. PCT/US2012/062702 dated Feb. 6, 2013.

Monetrey, Jacques, "PCL: Conservative Treatment", 4th Advanced Course on Knee Surgery, Jan. 22-27, 2012. http://www.kneecourse.com/download/seminar_2012/monday/MENETREY%20Conservative%20treatment.pdf.

Extended European Search Report from EP Application No. 12150517.6, May 22, 2012.

Smith, Sean D. et al., "Functional bracing of ACL injuries: current state and future directions", Knee Surgery Sports Traumatology Arthhroscopy, Springer, Apr. 27, 2013, 11 pages.

International Search Report and Written Opinion of the International Searching Authority from International Application No. PCT/US2014/013245, mailed May 6, 2014.

International Search Report from corresponding International Application No. PCT/US2014/042989, Oct. 15, 2014.

Jansson, Kyle S. et al., "A Historical Perspective of PCL Bracing", Knee Surgery Sports Traumatology Arthroscopy, Springer-Verlag, May 24, 2012, 7 pages.

* cited by examiner

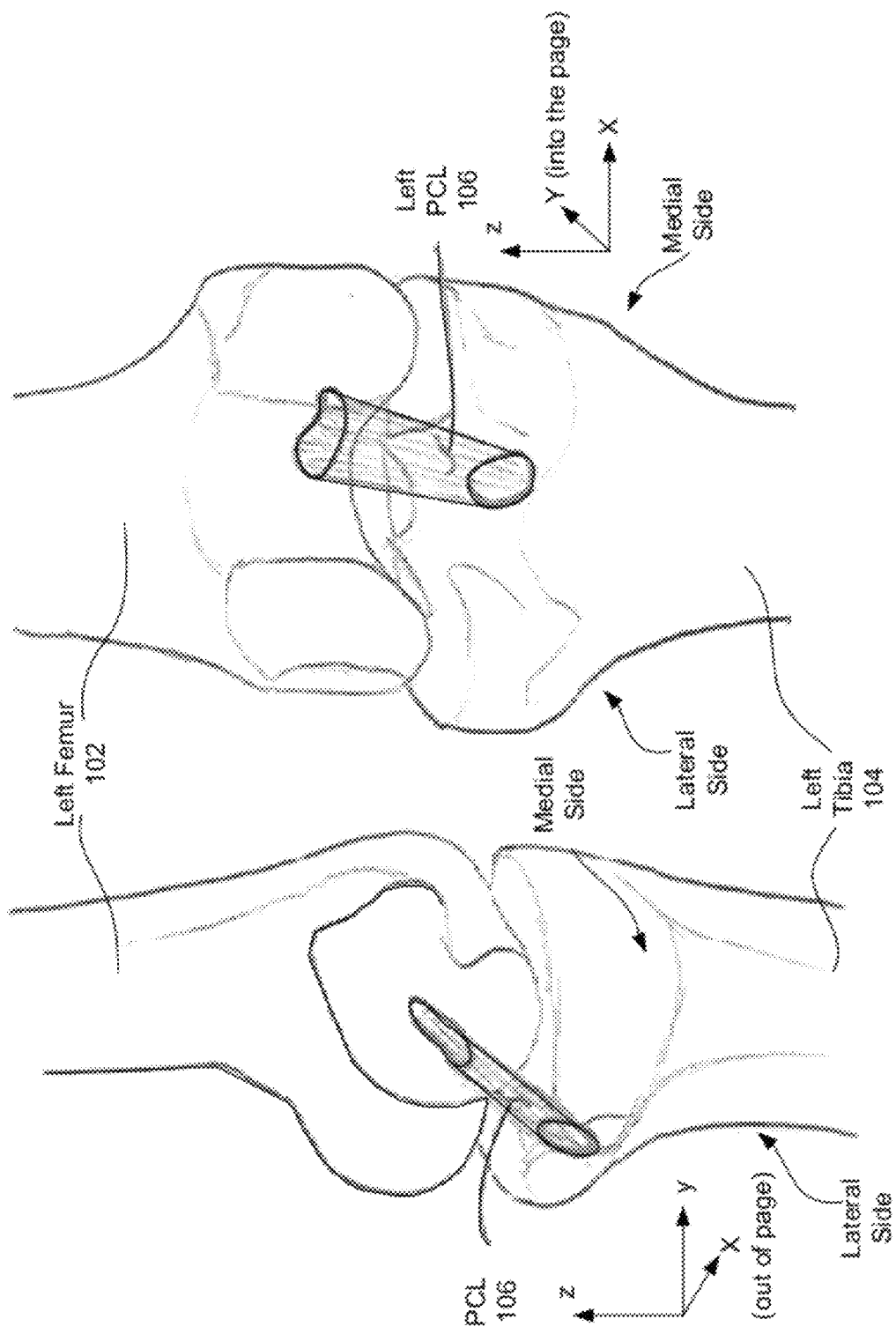

POSTERIOR CRUCIATE LIGAMENT SUPPORT BRACE

PRIORITY AND RELATED APPLICATIONS

This application claims priority to U.S. Patent Application No. 61/383,432 filed on Sep. 16, 2010, and incorporated herein by reference.

FIELD OF THE INVENTION

The present disclosure relates generally to orthopedics. In particular, but not by way of limitation, the present disclosure relates to systems, methods and apparatuses for a knee brace resisting knee flexion with a force that depends on the flexion angle.

BACKGROUND

The orthopedic medical field frequently recommends that patients use a variety of knee braces to support the knee during everyday activities following an orthopedic injury to the knee, for instance to the posterior cruciate ligament (PCL). PCLs are often damaged by sports activities, automobile crashes, and various other accidents.

The PCL is one of the primary stabilizing structures of the knee, providing stability during motion between the femur and tibia. When the PCL is damaged or torn, the knee is considered somewhat unstable. During this unstable time, it is possible to cause further damage to surrounding ligaments and structures in the knee with normal activity. A reconstruction surgery is usually recommended to replace the damaged or torn PCL and any other damaged internal knee structures by a qualified orthopedic surgeon. A reconstruction surgery will take place following the injury; surgeons often recommend waiting a minimum of two weeks before surgery as long as there is not also concern with secondary nerve damage. During these two weeks following the injury and prior to surgery, the patient's knee can be swollen, stiff, unstable and weak in certain areas of the knee joint and may not have its entire range of motion. In the cases with no nerve damage, it may beneficial to wait for surgery for the knee joint to regain the original range of motion back and develop strength in muscles which can be critical for the initial phase of post-surgical rehabilitation and recovery following surgery to help the knee joint heal.

If a substantial amount of time passes while the knee is unstable following the injury, but prior to surgery, the injury can become chronic. An acute knee injury is considered easier to repair and has a better chance of a positive post-surgery result, if repaired within 0-3 weeks of the injury, on average. A chronic injury is on average longer than 3 weeks old, is more difficult for the surgeon to repair, and typically yields a worse outcome following surgery. A proper knee brace, with proper function, can potentially improve stability to the knee during the time that a patient has an injury to their PCL.

In the case of PCL reconstruction surgery, the knee joint can be unstable for months while the ligaments, tissues, muscles, and other structures heal. Using a proper PCL brace after surgery can improve patient outcomes and decrease the amount of time to heal by stabilizing and supporting the knee.

SUMMARY OF THE INVENTION

Exemplary embodiments of the present invention that are shown in the drawings are summarized below. These and other embodiments are more fully described in the Detailed Description section. It is to be understood, however, that there is no intention to limit the disclosure to the forms described in this Summary of the Disclosure or in the Detailed Description. One skilled in the art can recognize that there are numerous modifications, equivalents and alternative constructions that fall within the spirit and scope of the disclosure as expressed in the claims.

Some embodiments of the disclosure can be characterized as an apparatus for bracing a knee, comprising a first portion, a second portion, and a coupling element. The first portion can be configured to engage with a first region of a leg, while the second portion can be configured to engage with a second region of the leg. The coupling element can be configured to couple the first portion to the second portion. The coupling element can also resist flexion with an anterior force on the posterior of the second region of the leg.

Some embodiments of the disclosure can be characterized as an apparatus for bracing a knee, comprising a first portion, a second portion, and a coupling element. The first portion can be configured to engage with a first region of a leg, while the second portion can be configured to engage with a second region of the leg. The coupling element can be configured to couple the first portion to the second portion such that the second portion can rotate about an axis and rotate relative to the first portion as a flexion angle changes. The coupling element can also resist flexion with an anterior force on the posterior of the second region of the leg, where the anterior force is nonlinearly related to the flexion angle.

Other embodiments of the disclosure may also be characterized as a method of bracing a knee. The method can include providing a first torque, on a posterior of a leg's shank, when a first knee flexion angle is 0°. The method can further include providing a second torque, greater than the first torque, on the posterior of the leg's shank, when a second knee flexion angle is between 0° and 105°. The method can also include providing a third torque, less than the second torque, on the posterior of the leg's shank, when a third knee flexion angle is greater than 105°.

Still further embodiments of the disclosure may be characterized as a method of bracing a knee. The method may include providing a first anterior force on a posterior location of a shank when a knee is at a flexion angle of 0°. The method may further include providing a second anterior force on the posterior of the shank when the knee is at a second flexion angle between 0° and 30°, wherein the second anterior force is less than the first anterior force. Still further, the method may include providing a third anterior force on the posterior of the shank when the knee is at a third flexion angle between the second flexion angle and 110°, wherein the third anterior force is greater than the first anterior force. The method may also include providing a fourth anterior force on a posterior of the shank when the knee is at a fourth flexion angle greater than the third flexion angle, wherein the fourth anterior force is less than the third anterior force.

BRIEF DESCRIPTION OF THE DRAWINGS

Various objects and advantages and a more complete understanding of the present disclosure are apparent and more readily appreciated by referring to the following detailed description and to the appended claims when taken in conjunction with the accompanying drawings:

FIGS. 1A and 1B illustrate two views of a left femur, a left tibia, and a left posterior cruciate ligament (PCL) along with their locations and shapes.

DETAILED DESCRIPTION

In general, aspects disclosed herein improve upon prior post-PCL-injury knee braces by using a dynamic rather than static force to resist knee flexion. This dynamic force creates better knee stability through the full range of knee flexion since the dynamic force better replicates the forces of a healthy PCL. This way, before or after surgery, the knee can feel stable without a healthy PCL, the user can avoid further damage to surrounding structures, and the brace improves recovery time, outcomes, and patient satisfaction.

Figure 11:
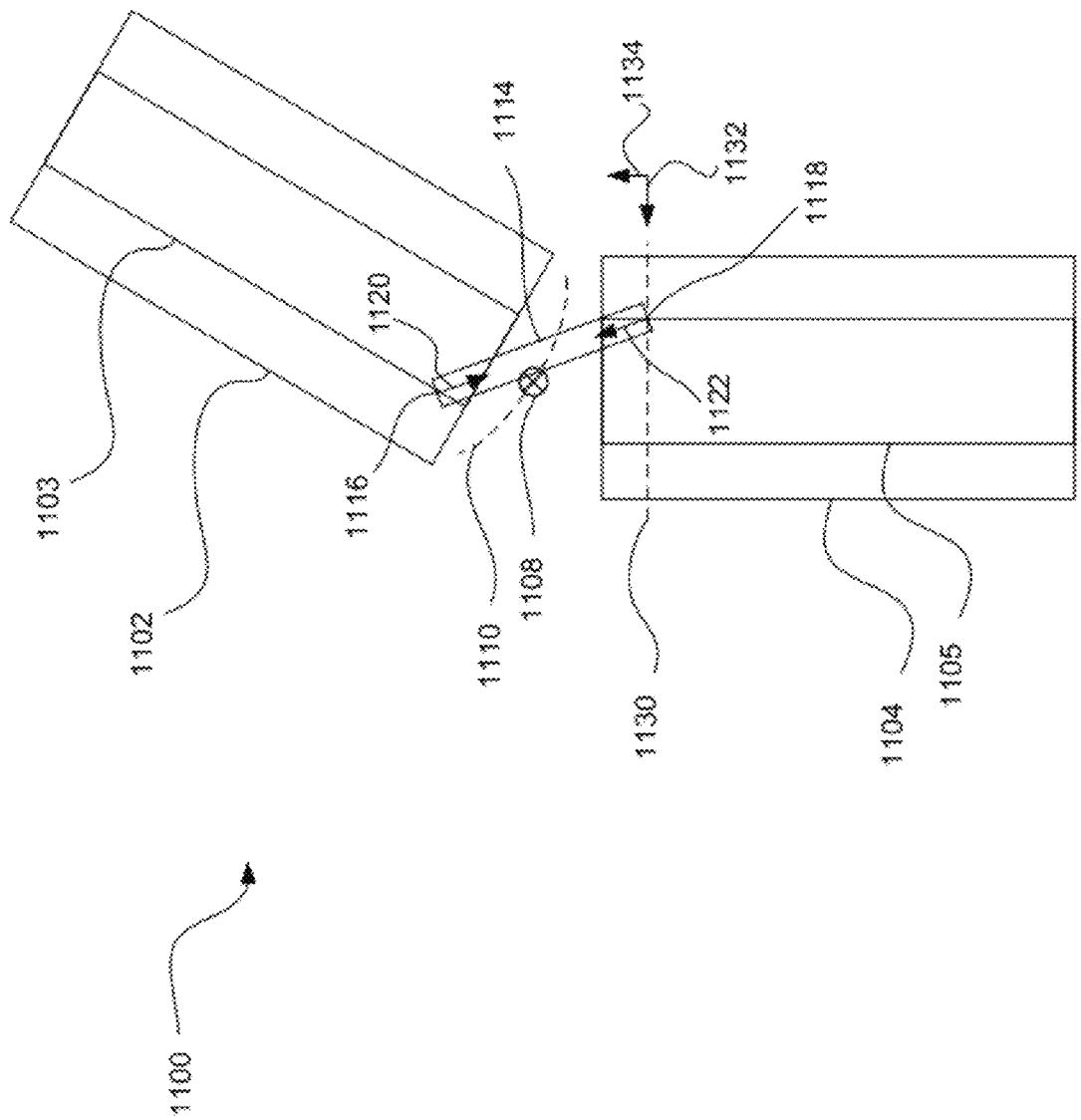
FIG. 11 is a simplified cross section of a leg including a thigh, femur, shank, tibia, and PCL.
Figure 12:
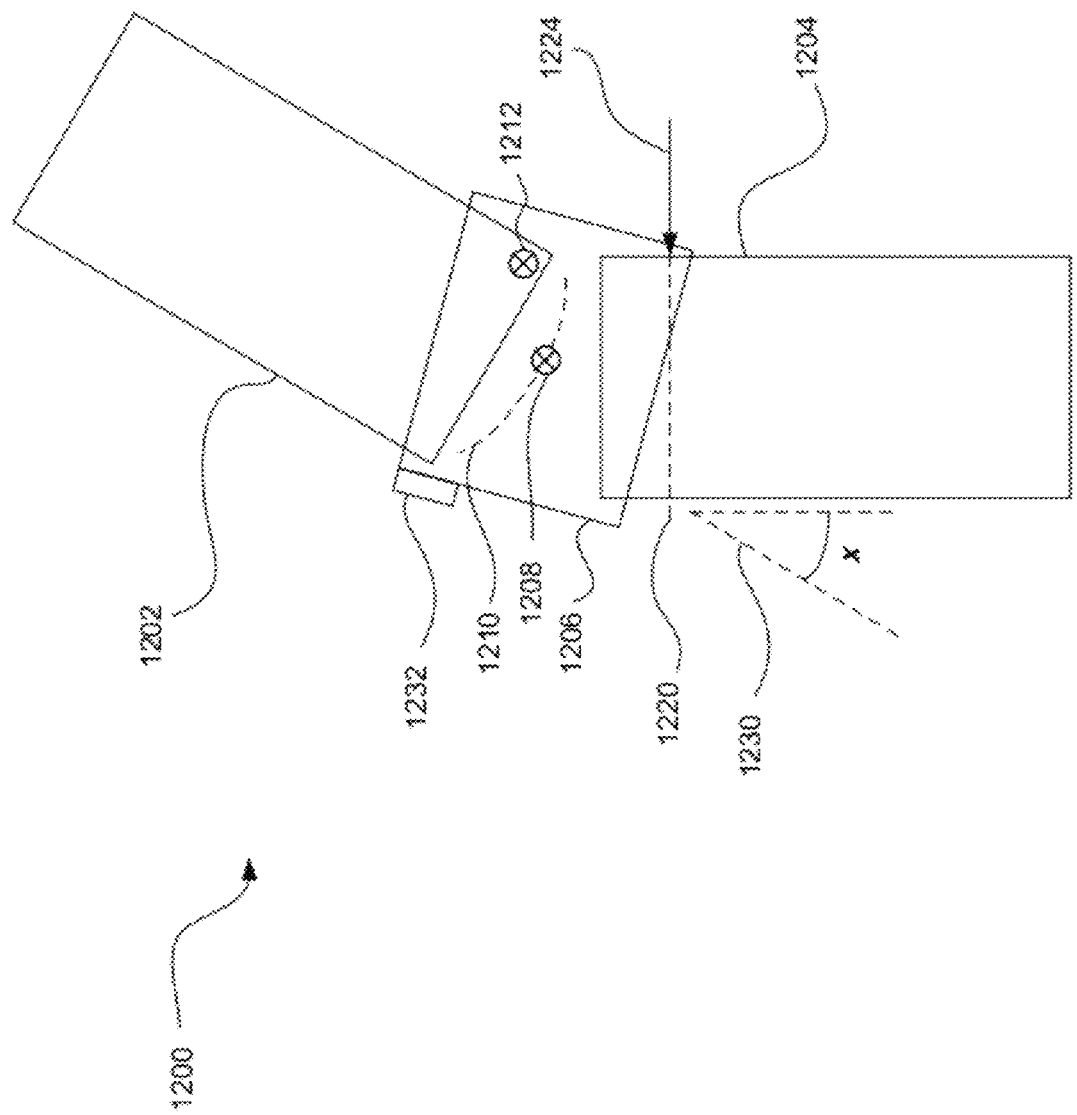
FIG. 12 illustrates one embodiment of a knee brace constructed in accordance with aspects of the present invention configured for application to a leg such as that illustrated in FIG. 11.

FIG. 12 illustrates one embodiment of a knee brace 1200 configured for application to a leg 1100 such as that illustrated in FIG. 11. The knee brace 1200 includes a first portion 1202, a second portion 1204, and a coupling element 1206. In the following description the first portion is referred to as the thigh portion and the second portion is referred to as the shank portion. The thigh portion 1202 is configured to engage with, couple to or wrap around a thigh 1102 (see FIG. 11 for all references to leg anatomy), and the shank portion 1204 is configured to engage with, couple to or wrap around a shank 1104. The coupling element 1206 is configured to couple the thigh portion 1202 to the shank portion 1204 and generate an anterior force 1224 that is applied to a posterior of the shank 1104 to resist leg 1100 flexion. The coupling element 1206 is also configured to enable the shank portion 1204 to rotate about a fixed axis 1212 or a moving axis 1208 as a flexion angle 1230 changes. The coupling element 1206 also enables the shank portion 1204 to rotate relative to the thigh portion 1202 as the flexion angle 1230 changes. The coupling element 1206 resists flexion, or changes in the flexion angle 1230, by applying the anterior force 1224 to the posterior of the shank 1104. The anterior force 1224 can be nonlinearly related to the flexion angle 1230, for instance via a second or third-order polynomial.

The knee brace 1200 is configured to support a leg 1100 during recovery from a PCL injury. The PCL 1114 is a ligament that generates a femoral PCL force 1120 relatively on the central-inferior-anterior location of the femur 1103 at the PCL-femur attachment site 1116 (where the PCL 1114 connects to the femur 1103), and generates a tibial PCL force 1122 on the superior-posterior location of the tibia 1105 at the PCL-tibia attachment site 1118 (where the PCL 1114 connects to the tibia 1105). The PCL 1114 connects to the tibia 1105 near a posterior surface of the tibia 1105 and near the tibial plateau 1130. The tibial PCL force 1122 has a vertical component 1134 and a lateral component 1132. By knowing the position of the PCL-tibia attachment site 1118, and a vector description of the PCL 1114 orientation, the vertical and lateral components 1134, 1132 of the tibial PCL force 1122 can be determined. Embodiments of knee braces in this disclosure replicate the anterior-posterior lateral component 1132 of the tibial PCL force 1122.

In FIG. 12, the anterior force 1224 on the shank 1104 is directed anteriorly along the tibial plateau 1220 (1130 in FIG. 11) just as the lateral component 1132 of the tibial PCL force 1122 is directed. However, while the anterior component 1132 of the tibial PCL force 1122 is concentrated at the PCL-tibia attachment site 1118, the anterior force 1224 can be localized or distributed. For instance, the shank portion 1204 may include a wrap or a cupped coupling portion able to distribute the anterior force 1224 across a broad surface area. Whatever embodiment the shank portion 1204 takes, the anterior force 1224 along the tibial plateau 1220 can replicate the lateral component 1132 of the tibial PCL force 1122.

The coupling element 1206 generates the anterior force 1224 via any of a variety of variable-resistance or variable-force mechanisms (e.g., spring, elastic band, four-bar linkage, to name a few non-limiting examples). Whatever the mechanism, the coupling element 1206 imparts an anterior force 1224 that nonlinearly depends upon the flexion angle 1230, where the flexion angle 1230 is an angle made between the thigh portion 1202 and the shank portion 1204 and has a value of 0° at extension (thigh and shank portions 1202, 1204 parallel) and has a value of 105° when the thigh and shank portions 1202, 1204 are nearly perpendicular.

While the anterior force 1224 is illustrated as being parallel to the tibial plateau 1220, the anterior force 1224 may be a lateral component of a force that is not parallel with the tibial plateau 1220. For instance, the shank portion 1204 may direct an angled force on the shank 1104, where the force is directed at an angle to the tibial plateau 1220, and the angled force is greater than the anterior force 1224. However, as the angled force would be greater than the anterior force 1224, the component of the angled force directed along the tibial plateau 1220 would equal the anterior force 1224. This example shows that various mechanisms can be used to generate the anterior force 1224, even if done indirectly as in this example.

The knee brace 1200 can be designed to impart the anterior force 1224 such that the anterior force replicates the anterior component 1132 of the tibial PCL force 1122, where the tibial PCL force 1122 is measured from one or more real PCLs. For instance, cadavers can be robotically manipulated to simulate a human body in motion, and force measurements (e.g., via force transducers) can be made to measure the PCL forces on the cadaverous PCL. Such measurements are preferably made using healthy reference PCLs—those that have been screened in order to weed out PCLs that may be less than ideal in terms of strength, flexibility, and other factors.

In an embodiment, the knee brace 1200 is designed to achieve anterior forces 1224 as a function of flexion angle 1230 that replicate the lateral component 1132 of the tibial PCL force 1122 to within plus or minus a margin of error measured for a range of flexion angles 1230 or for the full range of flexion angles 1230. For instance, the margin of error can be taken as an average over the range of flexion angles from 0° to 120°. In one embodiment, the margin of error can be plus or minus 30 N, 20 N, 15 N, 10 N, or 5 N. The tibial PCL force 1122 that the anterior force 1224 is compared to in order to determine the margin of error can be measured using one or more healthy reference PCLs. For instance, an average tibial PCL force 1122 for a plurality of healthy reference PCLs can be used.

The anterior force 1224 can be nonlinearly related to the flexion angle 1230 and this nonlinear relation can be adjusted via a force multiplier that can, for instance, be adjusted or controlled via a controller 1232. The force multiplier can have an equivalent effect on the anterior force 1224 for all flexion angles 1230 (e.g., a constant multiplied by a polynomial describing the nonlinear relation). The controller 1232 can be coupled to the coupling element 1206 as illustrated, but can also be coupled to the thigh portion 1202, the shank portion 1204, or a combination of the above. The controller 1232 can be a mechanical device (e.g., hydraulic and pneumatic, to name two) or an electromechanical device. For instance, the controller 1232 can rotate to tighten one or more cables, gears, cams, or elastic bands thereby increasing the anterior force 1224 for all flexion angles 1230. The controller 1232 can be controlled via a user's hand or fingers or alternatively via remote means wirelessly communicated to the controller 1232.

In one embodiment, the adjustable force multiplier, via the controller 1232, can be adjusted to account for a user's activity. For instance, the controller 1232 may have two or more settings for different user activities such as walking, running, high-intensity sports, lifting of heavy objects, and sleeping, to name just a few examples. The user can adjust the controller 1232 in order to adjust the force multiplier which increases the anterior force 1224 through the entire range of flexion angles 1230. In other words, by adjusting the controller 1132, and hence the adjustable force multiplier, a user can cause the knee brace to exert more or less of an anterior force 1224 than needed to replicate the forces exerted by a real and healthy PCL. In doing so, the user can tailor the knee brace 1200 to the user's current activity.

Such adjustments may also be useful to account for healing of the PCL. While the knee brace 1200 is meant to largely or entirely eliminate any loading of the PCL immediately after an injury or surgery, as the PCL heals it may be desirable to allow the PCL to begin taking on some portion of the loading—in other words, splitting the loading between the PCL and the knee brace 1200. For instance, as the PCL heals, the controller 1232 can be used to periodically decrease the anterior force 1224 via decreasing the adjustable force multiplier.

The adjustable force multiplier can also be used to tailor the knee brace 1200 to user characteristics such as age, weight, and gender, to name just a few. A user's healthy PCL may generate different forces than the reference PCLs used to design the knee brace 1200, and therefore the controller 1232 can be used to initially modify the knee brace 1200 to fit different users. For instance, the controller 1232 may be used to decrease the adjustable force multiplier, and hence the anterior force 1224, for users over a certain age or within a certain age range and with a certain strength. There may also be a different setting for each of multiple age ranges. Different knee braces can be sized to fit different patients and thus the force multiplier may also be used to account for different sizes of knee brace. There may also be different controller 1132 settings accounting for differences between typical male and female PCLs and users having different weights. Any two or more of these user characteristics as well as others can be combined to determine a setting for the controller 1232 that can be initially used to tailor the knee brace 1200 to the user.

While these settings can be separate from settings used to account for different user activities, or to account for PCL healing, there may also be a single setting that accounts for all of the above. For instance, a controller 1232 having twenty different positions, may be decreased two positions to account for a user's age (e.g. a user over 45 years old) increased three notches to account for the user's current activity (e.g. running) and decreased one notch to account for the user's gender (e.g. female). The net result would be a setting that is exactly the same as the factory position. However, were this user to stop running and adjust the controller 1232 to account for a new activity, for instance, walking, then the controller 1232 might be decreased two positions such that it was two positions lower than the factory-set position.

Alternatively, some of the controller 1232 settings can be controlled via a medical expert familiar with the user. In another embodiment, there can be settings on the controller 1232 controlled by a medical expert (e.g., accounting for weight, age, gender, and the extent of PCL healing) while one or more other settings on the controller 1232 are controlled by the user (e.g., user activity). In another embodiment, there may be more than one controller 1232, one available for medical expert control and one available for user control.

The illustrated location, shape, and size of the controller 1232 are not meant to limit the controller 1232 in any way. For instance, the controller 1232 can be arranged on a lower edge of the coupling element 1206 and be larger or more square or more round than illustrated, to name just a few non-limiting examples of how the controller 1232 can take on different shapes, locations, and sizes.

In one embodiment, the relation of the anterior force 1224 to the flexion angle 1230 can be described via a polynomial, such as the third-order polynomial that follows:

$$Y=\epsilon(-0.00017x^3+0.0236x^2+0.0397x+13.1) \quad \text{(Equation 1)}$$

In Equation 1, Y is the anterior force 1224 (in Newtons) on the shank 1104, x is the flexion angle 1230 (in degrees), and $\epsilon$ is the adjustable force multiplier. As seen, the adjustable force multiplier c does not change the shape or curvature of the polynomial of Equation 1, but rather acts to increase or decrease an amplitude of the curve for the full range of knee motion. Although $\epsilon$ is a fixed value in Equation 1, in other embodiments, $\epsilon$ can depend on flexion angle x (1230).

As seen by the third-order polynomial of Equation 1, the anterior force Y (or 1224) increases as a function of increasing flexion angle x (or 1230) until a first angular threshold (~105°) is reached at which point the anterior force Y (1224) begins to decrease as a function of increasing flexion angle x (1230). Furthermore, below a second angular threshold (less than the first angular threshold), the anterior force Y (1224) decreases as a function of increasing flexion angle x (1230).

In an embodiment, the first angular threshold is between 100° and 110°. In another embodiment, the first angular threshold is 105°. In another embodiment, the first angular threshold is at an angle equal to a largest of the three roots of Equation 1. In yet another embodiment, the second angular threshold is between 0° and 10°. In a further embodiment, the second angular threshold is 5°. In another embodiment, the second angular threshold is at an angle equal to a root of Equation 1 that is less than the largest of the three roots but greater than the smallest of the three roots.

The thigh portion 1202 can include any number of different components, systems, or mechanisms for coupling to a thigh 1102 of the leg 1100. For instance, the thigh portion 1202 can include a wrap with structural members to couple the wrap to the coupling element 1206. The thigh portion 1202 can preferably be arranged to prevent movement between the thigh 1102 and the thigh portion 1202. The knee brace 1200 may present a torque on the thigh portion 1202 relative to the thigh 1102, and therefore the thigh portion 1202 can be designed to distribute the torque over a larger area of the thigh 1102. Although the thigh portion 1202 is illustrated as having a similar size to the thigh 1102, this is not required. The thigh portion 1202 can be designed with any shape and size that enables coupling to the shank portion 1204 via the coupling element 1206.

The shank portion 1204 can include any number of different components, systems, or mechanisms for coupling to a shank 1104 of the leg 1100. For instance, the shank portion 1204 can include a wrap with structural members to couple the wrap to the coupling element 1206. Alternatively, the shank portion 1204 can include a shank-coupling portion or element shaped like a half-pipe that couples to the shank 1104 merely via the anterior force 1224. The shank portion 1204 can preferably be arranged to prevent movement between the shank 1104 and the shank portion 1204. The knee brace 1200 may present a torque on the shank portion 1204 relative to the thigh 1102, and therefore the shank portion 1204 can be designed to distribute the torque over a larger area of the shank 1104. Although the shank portion 1204 is illustrated as having a similar size to the shank 1104, this is not required. The shank portion 1204 can be designed with any shape and size that enables coupling to the thigh portion 1202 via the coupling element 1206.

A typical leg 1100 includes a moving rotation axis 1108 about which the femur 1103 and tibia 1105 can rotate. This moving rotation axis 1108 tends to move along a path 1110 that can be curved (e.g., a cam-follower path), and may have one or more inflexion points (where the curvature passes through zero and reverses curvature). As such, the knee brace 1200 replicates this movement either by enabling the thigh portion 1202 and the shank portion 1204 to rotate about a fixed axis 1212 or about a moving rotation axis 1208. In either case, the axis 1208, 1212 can be arranged so as to replicate the axis 1108 of the leg 1100. The moving rotation axis 1208 can move along a path 1210 that replicates the path 1110 of a real leg 1100. There may even be two axes of rotation—one for the thigh portion 1202 and one for the shank portion 1204. The locations of the axes 1212, 1208 and the location and shape of the path 1210 are illustrative only, and in other embodiments can replicate to a substantial extent, the position and shape of real axes of rotation and path shape and size of the leg 1100.

A more detailed description of the PCL, the studies associated with PCL forces, and a particular embodiment of a knee brace will now be discussed. The PCL is a ligament which is connected to the superior-posterior and somewhat medial aspect of the tibia and the central inferior aspect of the femur. The ligament function is analogous to a mechanical spring (which is also analogous to a two-force member) between the tibia and femur, and provides stability by providing tension to connect the bones. Primarily tension, rather than a moment, is applied between the two bone structures from this ligament.

FIGS. 1A and 1B illustrate two views of a left femur 102, a left tibia 104, and a PCL 106 along with their locations and shapes. In particular, FIGS. 1A and 1B show the relative attachment sites and shape of the PCL 106 on a left tibia 104 and femur 102 of a knee at 0° flexion. Recent research has tracked the locations of these attachment sites from maximum extension to maximum flexion (maximum bending of the knee).

The locations of these attachment sites can be plotted in x-y-z three-dimensional space according to the coordinate planes shown in FIGS. 1A and 1B. In both figures, the z direction is vertical while the x and y directions are horizontal. In FIG. 1A the y direction is parallel to the page and the x direction is pointed out of the page. In FIG. 1B the y direction is pointed into the page and the x direction is parallel to the page.

Additional research has indicated what force the ligament presents to the tibia 104 and femur 106 at various positions on the tibia 104 and femur 106 for various flexion angles of the knee (the PCL 106 presents primarily tension forces rather than moments). For instance, a force-measuring instrument (e.g., load gauge, strain gauge, load cell or load gauge) can be affixed to either end of the PCL 106 (e.g., via drilling into the bone at an attachment site and inserting a force-measuring instrument attached to an end of the PCL 106) and used to measure the force exerted by the PCL 106 at the attachment site. These forces, when matched with the location of the PCL 106 and knowledge of the PCL 106 structure, are used to determine force vectors that the PCL 106 applies to the femur 102 and tibia 104 for different knee flexion angles.

Some exemplary forces, as a function of flexion angle and PCL 106 position (relative to the tibia 104), are shown in Table 1 for five knee flexion angles. Table 1 was created from measurements of healthy PCLs 106. From this data, the positional unit vector of the force from the PCL 106 onto the tibia 104 is calculated. From research measuring the in situ PCL 106 force on the tibia 104 for different knee flexion angles, this can be matched with the unit vector of the position of the PCL 106 relative to the tibia 104 to know the force and direction of the PCL 106 onto the tibia 104.

Figures 2A, 2B:
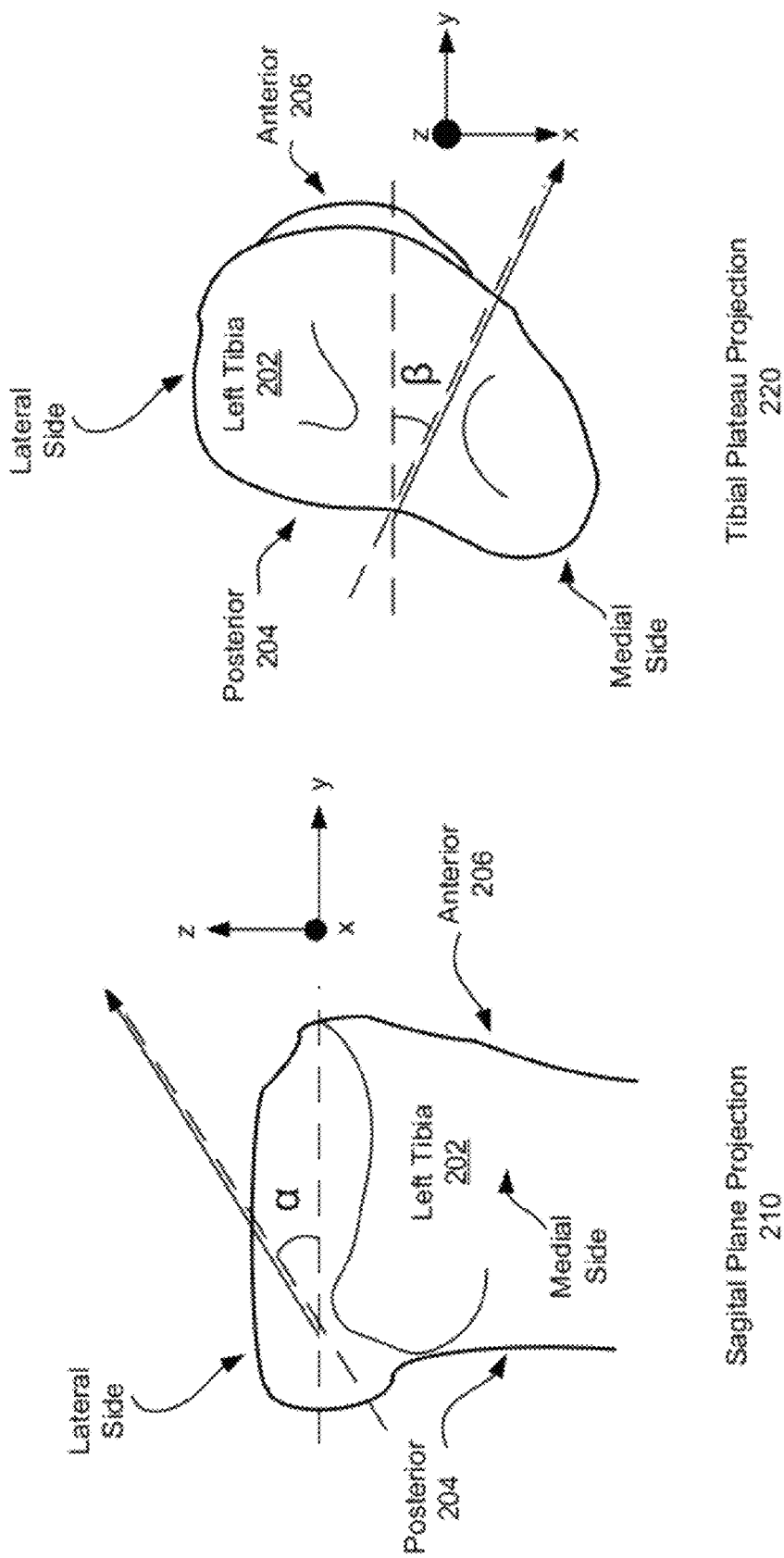
FIG. 2A illustrates a profile view of a top portion of a left tibia.
FIG. 2B illustrates a top-down view of a left tibia.

The PCL position in Table 1 describes the location of the PCL 106 for different knee flexion angles. The PCL 106 angular orientation can be understood in the context of FIGS. 2A and 2B. The elevation angle a shown in Table 1 is also illustrated in FIG. 2A in the sagittal plane 210, and is an angle of the PCL 106 measured from the tibial plateau (x-y plane) towards the z-axis. The internal deviation angle β is illustrated in FIG. 2B parallel to the tibial plateau 220, and is an angle of the PCL 106 measured from the sagittal plane (y-z plane) towards the x-axis. For greater accuracy in developing a knee brace, a greater number (higher resolution) of knee flexion angles than measured for Table 1 could be taken into account.

TABLE 1

PCL Force and Position for a variety of knee flexion angles.

| | | Knee Flexion Angle [deg] | | | | |
|---|---|---|---|---|---|---|
| | | 0 | 30 | 60 | 90 | 120 |
| In Situ PCL Force | [N] | 30.5 | 82.3 | 114.2 | 126.6 | 107.7 |
| | [lbf] | 6.9 | 18.5 | 25.7 | 28.5 | 24.2 |
| PCL Angular Orientation [deg] | Elevation angle α (Sagittal Plane) | 49.6 | 46.1 | 48.9 | 54.0 | 64.6 |
| | Internal Deviation β (Tibial Plateau) | 20.5 | 7.7 | 12.3 | 12.1 | 28.5 |
| Force [lbf] | Y Axis (Anterior to Posterior) | 1.01 | 2.92 | 3.84 | 3.80 | 2.36 |
| | X Axis (Medial to Lateral) | 0.38 | 0.39 | 0.84 | 0.82 | 1.28 |

TABLE 1-continued

PCL Force and Position for a variety of knee flexion angles.

| | | Knee Flexion Angle [deg] | | | | |
|---|---|---|---|---|---|---|
| | | 0 | 30 | 60 | 90 | 120 |
| | Z Axis (Inferior to Superior) | 1.19 | 3.03 | 4.40 | 5.23 | 4.97 |
| PCL Position (Unit Vectors) | y | 0.63 | 0.69 | 0.65 | 0.58 | 0.42 |
| | x | 0.24 | 0.09 | 0.14 | 0.13 | 0.23 |
| | z | 0.74 | 0.72 | 0.75 | 0.80 | 0.88 |

Figure 3B:
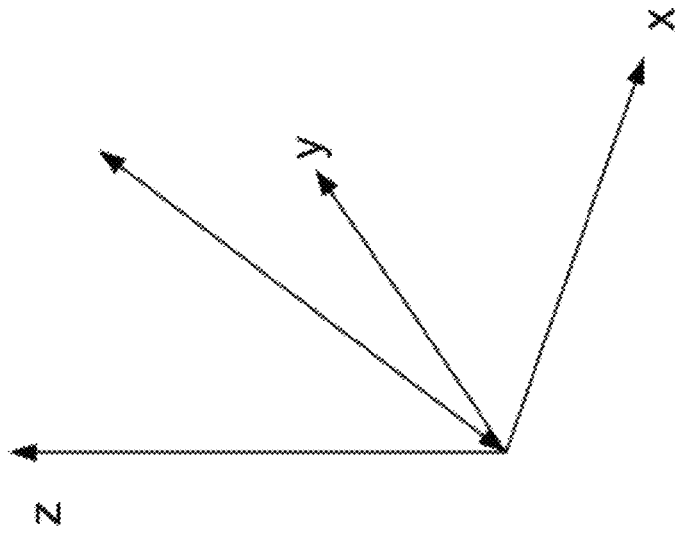
FIG. 3B illustrates a force vector in x-y-z space representative of the force exerted by a measured PCL.
Figure 3A:
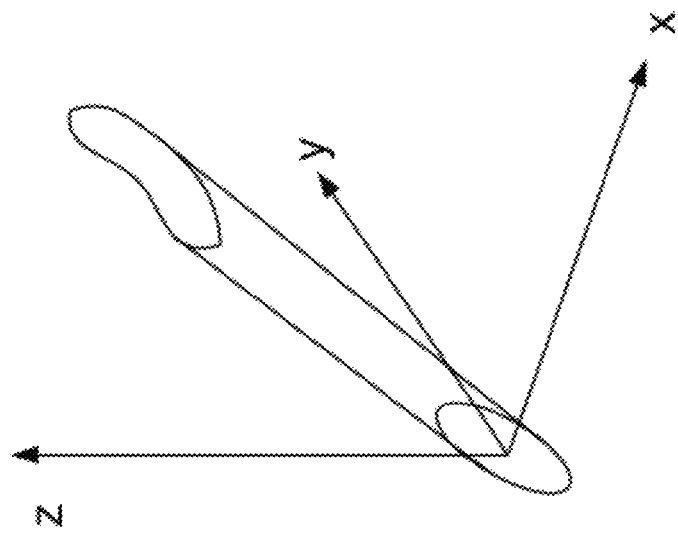
FIG. 3A illustrates a PCL shape as projected in x-y-z space.

The forces calculated in Table 1 can be plotted in three dimensional space, such as FIG. 3B where a three-dimensional force vector is illustrated in x-y-z space to model the forces on and applied by the PCL illustrated in FIG. 3A.

Figure 4:
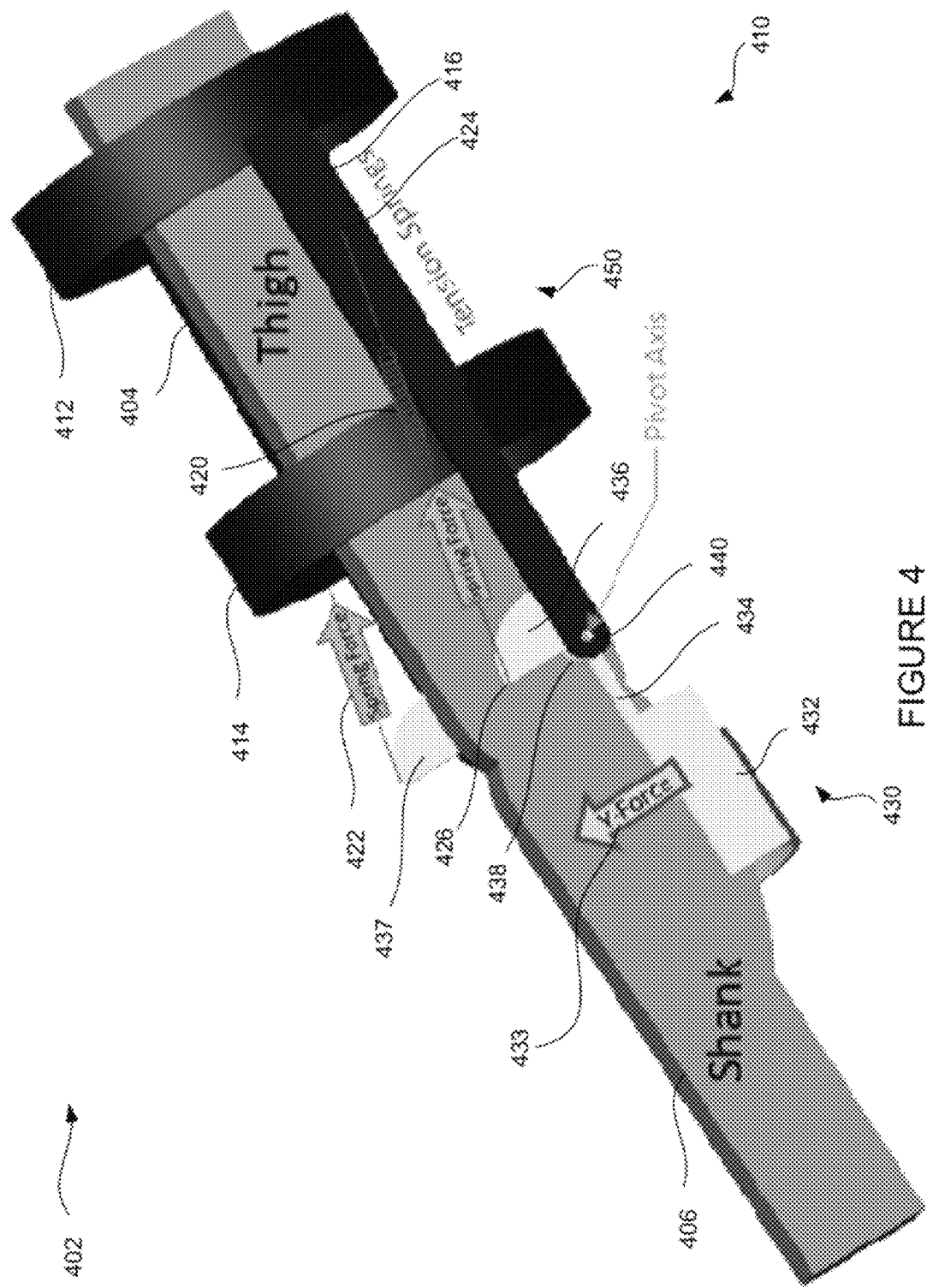
FIG. 4 illustrates a knee brace constructed according to one aspect of the present invention.

FIG. 4 illustrates a knee brace 410 constructed in accordance with one aspect of the present invention. The knee brace 410 can replicate the loads that a healthy PCL would place on the tibia. The knee brace 410 is arranged on a leg 402 having a knee at 0° flexion. The leg 402 comprises a shank 406 and a thigh 404. A back portion of the shank 406 is referred to as the calf, and the shank 406 has an anterior (front) and a posterior (back) portion. The knee brace 410 presents an anterior force 433 (directed from the posterior portion to the anterior portion) on the calf of the shank 406. The knee brace 410 can include a shank portion 430 coupled to a thigh portion 450 (e.g., a form fitting brace) at a pivot point 440. The thigh portion 450 can be wrapped around the thigh 404 and the shank portion 430 can be pressed against the posterior portion (or the calf) of the shank 406.

A spring 420, or spring-like mechanism, also couples a first spring attachment site 424 on the thigh portion 450 to a second spring attachment site 426 on the shank portion 430 where the first and second spring attachment sites 424, 426 are arranged at a first and second radius, respectively, from the pivot point 440. The spring 420 generates a torque (the anterior force 433) on the shank portion 430 around the pivot point 440, where this torque presses the shank portion 430 against the calf of the shank 406 in order to replicate the anterior force of a healthy PCL pulling on the tibia of the shank 406. This torque on the shank 406 can also be referred to as an anterior force 433 since it is directed anteriorly to the shank 406. The torque on the shank portion 430 varies depending on the flexion between the shank portion 430 and the thigh portion 450. In this way, the knee brace 410 presents a varying torque on the shank 406 relative to the thigh 404 replicating the varying forces that a healthy PCL presents to the shank 406 relative to the thigh 404 through the full range of knee motion.

Following surgery, the anterior force 433 will allow the new PCL to remain relatively unstressed during the initial healing of the PCL. The anterior force 433 from the knee brace 410 will substitute for what the PCL would otherwise apply to the tibia and femur. The anterior force 433 allows the knee to remain in the proper position and counteracts the force of gravity on the tibia, especially while the patient is sleeping. This will promote healing to the patient by reducing the load on the patient's PCL.

As the PCL heals, the anterior force 433 can be reduced to allow the PCL to take on a gradually increasing load over time. When the PCL is healthy and has healed rigidly following surgery, the brace 410 can be removed to allow the healed PCL to safely handle unaided loading. This will reduce patient pain and improve recovery time.

The springs 420 & 422 or spring-like mechanism can take a variety of embodiments. In particular, any mechanism will suffice that increases resistance to extension when stretched. In other words, the further apart the first and second spring attachment sites 424, 426 become, the greater the force 422 pulling the first and second spring attachment sites 424, 426 towards each other becomes. This force 422 can have a linear or non-linear dependency on the distance between the first and second spring attachment sites 424, 426. A tension spring and an elastic band are just two non-limiting examples of the spring 420.

It may be preferable to locate the first spring attachment site 424 near a center of gravity or center of torque on the thigh portion 450 such that the forces exerted by the spring 420 on the thigh portion 450 cause less torque on the thigh portion 450.

The spring 420 can be coupled to a second spring attachment site 426 on the shank portion 430 offset by a radius from the pivot axis 440, such that the spring force 422 applies a torque on the shank portion 430 that resists or pushes back against knee flexion.

The thigh portion 450 may include a first and second wrap 414, 412, where each wrap can encircle all or a portion of the thigh 404. The wraps 414, 412 can be coupled to each other by two wrap couplers 416. The first spring attachment site 424 for each spring 420 can be located on the respective wrap coupler 416. The wrap coupler 416 can also couple to the shank portion 430 at the pivot point 440. When the knee is extended, the spring 420 may not be parallel to the wrap coupler 416, however as the knee flexes, the spring 420 may approach, and in some embodiments, pass through parallel with the wrap coupler 416.

Figure 5:
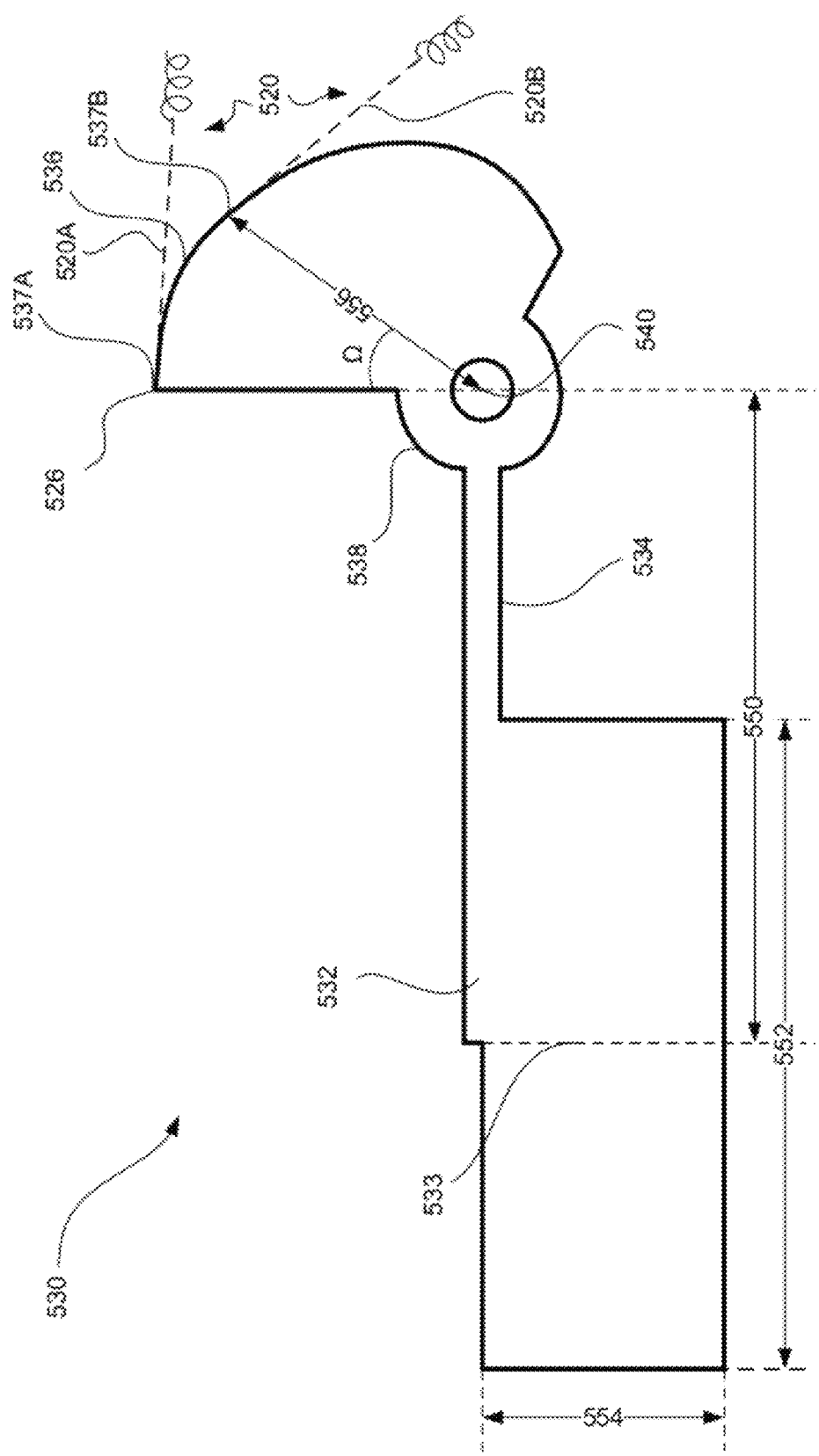
FIG. 5 illustrates a profile of one embodiment of a PCL brace shank portion.

FIG. 5 illustrates a profile of one embodiment of a shank portion 500. The shank portion 500 comprises at least a calf-coupling portion 532, and two splines 536. As this is a profile view, only one spline 536 is viewable. The calf-coupling portion 532 can be cupped or shaped like a portion of a tube such that the calf-coupling portion 532 is able to rest against and press against a calf. The calf-coupling portion 532 can be cupped or curved so as to be shaped to fit a calf. In other words, the calf-coupling portion 532 is shaped so as to rest against and/or press against a calf in a fashion that evenly distributes pressure across the portions of the calf in contact with the calf-coupling portion 532. The calf-coupling portion 532 can include padding or other material or coating to increase comfort of the calf-coupling portion 532. For instance, the calf-coupling portion 532 can include air holes, air vents, or air channels to assist in temperature and moisture control of the calf. The shank portion 530 may optionally include a bridge 534 coupled between the calf-coupling portion 530 and the spline 536. There may also be a pivot ring 538 centered on the pivot point 540. The pivot ring 538 may couple the optional bridge 534 to the spline 536 or the calf-coupling portion 532 to the spline 536 if no bridge 534 is used. The calf-coupling portion 532 may be a wrap or include a wrap.

The calf-coupling portion 532 can pivot around the pivot point 540 at a radius 550 measured from the pivot point 540 to a midpoint or midplane 533 of the calf-coupling portion 532. As the radius 550 increases, the anterior force 433, all else being equal, increases, while a decreased radius 550 results in a decreased anterior force 433. Thus, adjusting the radius 550 is one way to tailor the anterior force 433 to replicate the forces applied by a healthy PCL.

Although the calf-coupling portion 532 is illustrated as being separated from the pivot member 538 by a bridge 534, in variations, the calf-coupling portion 532 can be coupled directly to the pivot member 538 without the optional bridge 534.

The second spring attachment site 526 can be located on the spline 536 (e.g., as illustrated in FIG. 5). A first reference plane (dotted vertical line) can be considered that intersects both the second spring attachment site 526 and the pivot point 540. From this reference plane, an angle Ω exists, where the spline radius 556 decreases as Ω increases. As such, the point on the spline 536 where the spring 520 is tangent to the spline 536 (the tangent point 537) becomes ever closer to the pivot point 540 as the knee flexes. Because the radius 556 of the spline 536 decreases as Ω increases, as the knee flexes, the anterior force 433 increases in a non-linear fashion. Beyond a threshold angle (e.g., (105°) the anterior force 433 can decrease. For instance, a healthy PCL decreases the force on the tibia once the knee flexion passes 105°. Thus, the decreasing spline radius 556 as Ω increases, enables the knee brace to replicate the nonlinear forces that a healthy PCL imparts on the tibia and even the decreasing force that a healthy PCL imparts on the tibia once the knee flexes beyond a certain angle.

A spring 520 can be coupled to the second spring attachment site 526 via an elastic or inelastic portion. The elastic or inelastic portion is configured to bend and rest against the circumference of the spline 536. In the illustrated embodiment, the spring 520 is shown in a first position (520A) and a second position (520B). The first position 520A represents the spring 520 when the knee is at extension and the second position 520B represents the spring 520 when the knee is has a flexion angle Ω.

The elastic or inelastic portion wraps around the circumference of the spline 536 as the knee flexes (increasing Ω), and is directed away from the spline 536 at a first or second tangent point 537A, 537B. The first tangent point 537A is illustrated where the spring 520 in the first spring position 520A is directed away from the spline 536 and the second tangent point 537B is illustrated where the spring 520 in the second spring position 520B is directed away from the spline 536.

The spline radius 556 at the tangent point 537 corresponds to the anterior force 433 on the shank 406 since the spring force 422 applies a greater torque when the spline radius 556 is greater and a lesser torque when the spline radius 556 is lesser. Thus, as the knee flexes, the elastic or inelastic portion of the spring 520 wraps around the spline 536 circumference (clockwise in FIG. 5), the tangent point 537 moves clockwise in FIG. 5, and hence the spline radius 556 decreases. As the elastic or inelastic portion of the spring 520 wraps around the spline 536, the spring 520 is stretched, thus increasing the anterior force 433 on the shank. However, since the spline radius 556 corresponding to the tangent point 537 decreases at the same time, each angular increase in flexion results in a lesser increase in anterior force 433. This trend continues until at a certain knee flexion, increased flexion results in decreased anterior force 433 (e.g., when the knee flexes past ~105°).

The shape of the spline 536, or the variation in radius 556, can be based on calculations that account for a number of factors. First, the goal is to create a knee brace where the anterior force replicates that of a healthy PCL for different knee flexion. To achieve this goal a number of variables can be adjusted until the ratio of knee brace flexion to anterior force 433 of the calf-coupling portion 532 replicates the equivalent healthy PCL forces. These variables can include the following: spring 520 constant, initial spring 520 deformation (see 662 in FIG. 6), radius 550, length 552 of calf-coupling portion 532, height 554 of calf-coupling portion 532, position of the pivot point 540 relative to a pivot point of the knee, position of the first spring attachment site, position of the second spring attachment site 526, spline radius 556 as a function of angle Ω, and an amount of plastic deformation in the shank portion 530 and the thigh portion.

Some of these variables were measured with respect to a prototype knee brace for the knee flexion angles of 0°, 30°, 60°, 90°, and 120°, and these measured values a forth in Table 2. The desired force is a known force that a healthy PCL exerts on the tibia for each respective flexion angle. The achieved force was a measure of the anterior force 433 generated by the knee brace. The spring force (422 in FIG. 4) was a measured spring force for the springs of a knee brace. The length to force on calf was a measured distance 550 between the pivot point 540 and the midpoint or midplane 533 of the calf-coupling portion 532 illustrated in FIG. 5 for the tested knee brace. The spline radius was a measured spline radius 556 (see FIG. 5) for the tested knee brace. Spring displacement was a measure of the spring extension at the respective flexion angles.

The spring constant for all of the measurements in Table 2 was 4 lb/in, and the spring was extended 0.5 inches from equilibrium at extension (Ω=0°). Although only five flexion angles are shown in Table 2, future designs can be based upon a greater number of flexion angles and the respective data for each of those angles.

TABLE 2

Knee Brace Force for a variety of knee flexion angles and the results for the spline shape

| Knee Angle (Flexion) [deg] | Desired Force [lb] | Achieved Force [lb] | Spring Force [lb] | Length to Force on Calf [in] | Spline Radius [in] | Spring Displacement [in] |
|---|---|---|---|---|---|---|
| 0 | 1 | 1.00 | 2.00 | 4.0 | 2.00 | 0.50 |
| 30 | 2.9 | 2.90 | 6.03 | 4.0 | 1.80 | 1.61 |
| 60 | 3.8 | 3.80 | 9.04 | 4.0 | 1.56 | 2.45 |
| 90 | 3.8 | 3.80 | 10.82 | 4.0 | 1.28 | 2.96 |
| 120 | 2.4 | 2.40 | 10.03 | 4.0 | 0.85 | 2.83 |

FIGS. 6-10 illustrate the shank portion 530 along with a portion of a thigh portion for each of the flexion angles 0°, 30°, 60°, 90°, and 120°, respectively.

Figure 6:
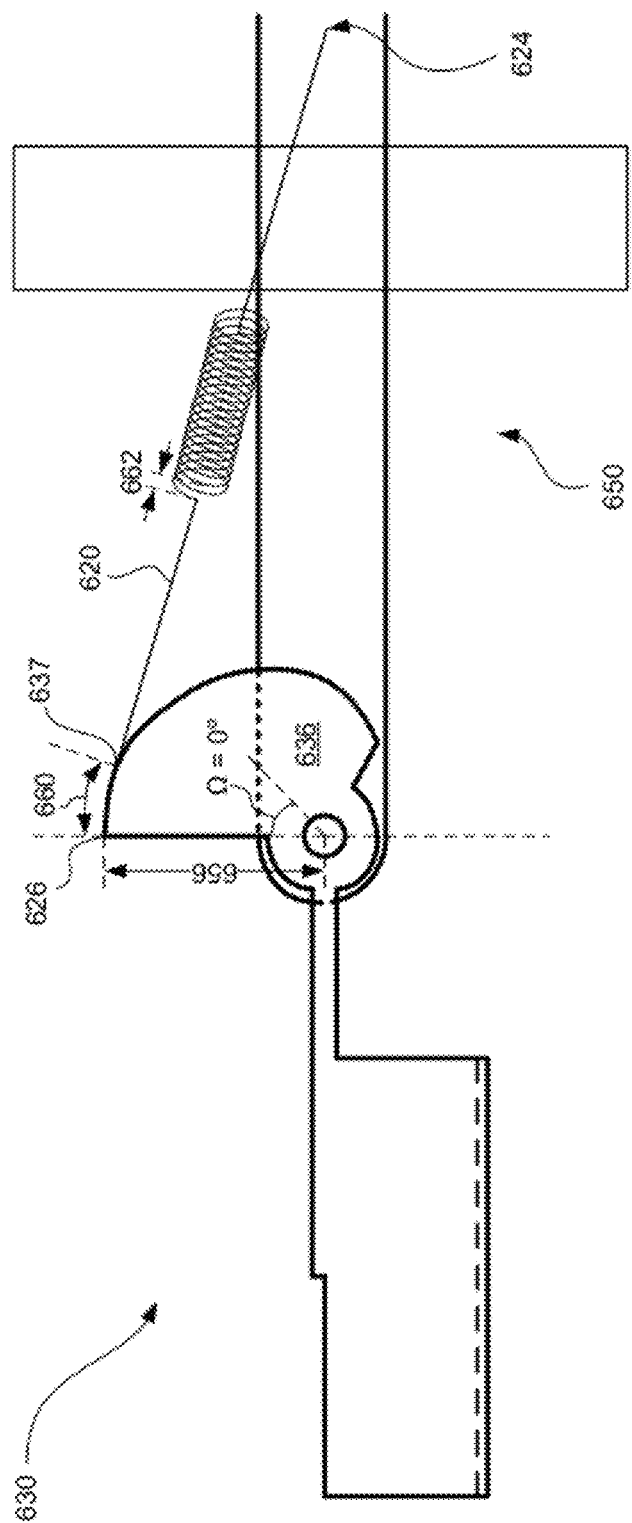
FIG. 6 illustrates a PCL brace shank portion coupled to a PCL brace thigh portion for a knee at extension ($\Omega=0°$).

FIG. 6 illustrates a shank portion 630 coupled to a thigh portion 650 for a knee at extension (Ω=0°). At extension, the spline radius 656 is greatest. The spring 620 couples to the shank portion 630 via the second attachment site 626 and couples to the thigh portion 650 via the first attachment site 624. The spring 620 has an initial displacement 662 and wraps around a portion of the spline circumference 660. The spring 620 is tangent with the spline circumference and separates from wrapping around the spline 636 at a tangent point 637.

While the spring displacement 662 shows the total displacement for the spring 620 rather than the actual location of the displacement. The actual spring displacement is distributed evenly through the spring 620.

Figure 7:
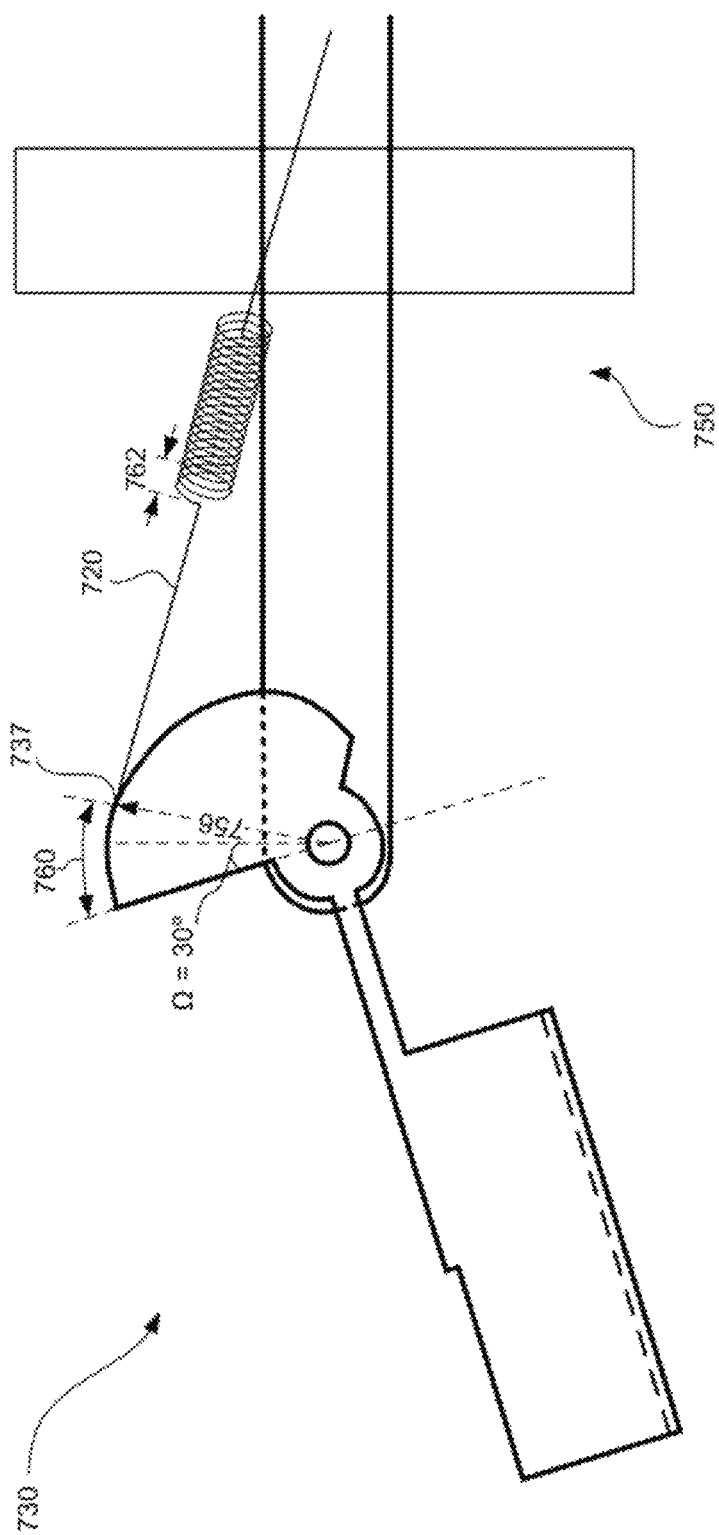
FIG. 7 illustrates a PCL brace shank portion coupled to a PCL brace thigh portion for a knee at a 30° flexion angle ($\Omega$).

FIG. 7 illustrates a shank portion 730 coupled to a thigh portion 750 for a knee at a 30° flexion angle (Ω). At a flexion angle of 30°, the spline radius 756 at the tangent point 737 is smaller than the spline radius 656 in FIG. 6. The portion of the spline circumference 760 around which the spring 720 has wrapped is increased compared to that in FIG. 6. The spring 720 also sees greater displacement 762 than in FIG. 6. The tangent point 737 has also moved.

Figure 8:
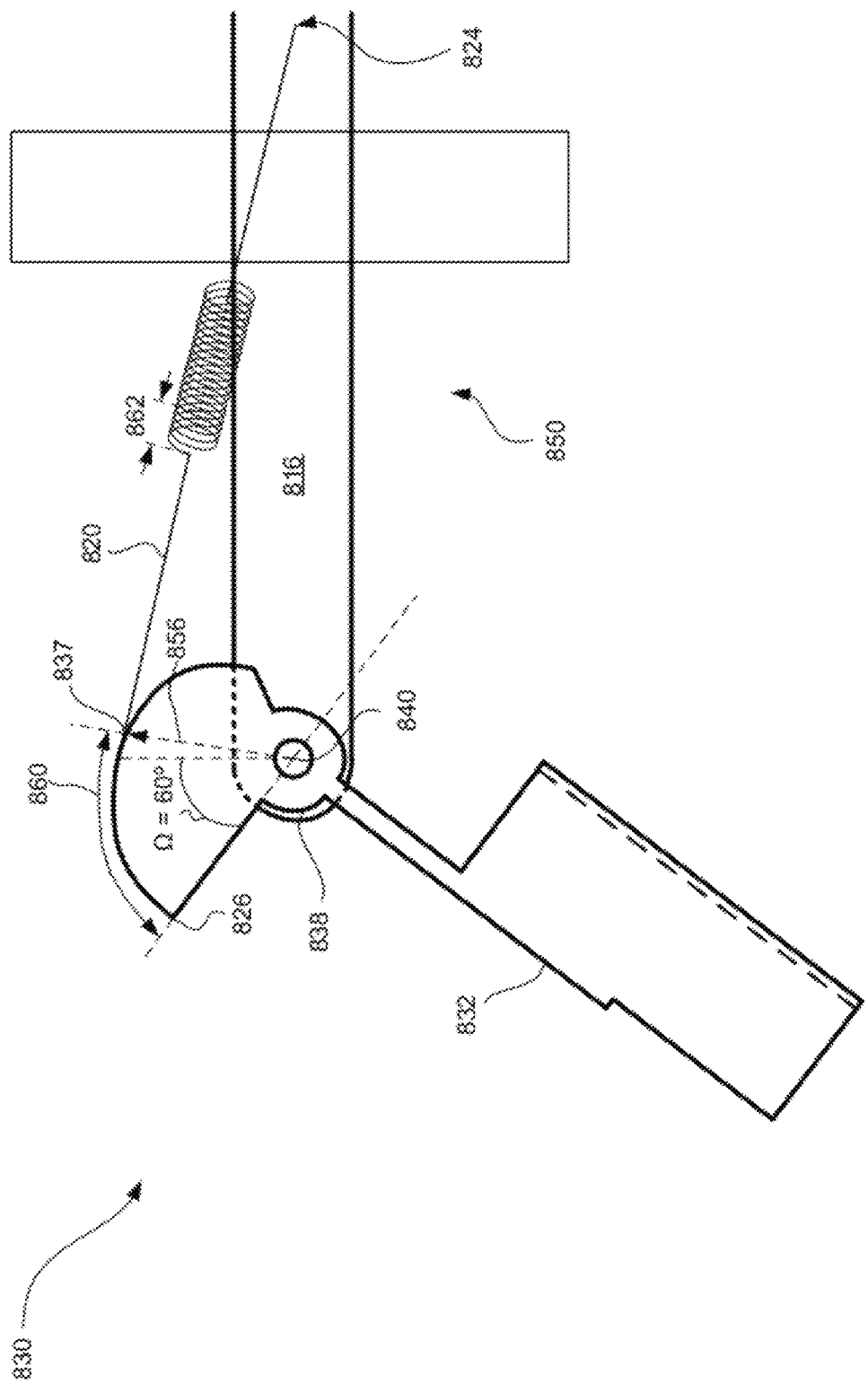
FIG. 8 illustrates a PCL brace shank portion coupled to a PCL brace thigh portion for a knee at a 60° flexion angle ($\Omega$).

FIG. 8 illustrates a shank portion 830 coupled to a thigh portion 850 for a knee at a 60° flexion angle (Ω). At flexion angle of 60°, the spline radius 856 at the tangent point 837 is smaller than the spline radius 756 in FIG. 7. The portion of the spline circumference 860 around which the spring 820 has wrapped is increased compared to that in FIG. 7. The spring 820 also sees greater displacement 862 than in FIG. 7, and the tangent point 837 is in a different location than in FIG. 7.

Figure 9:
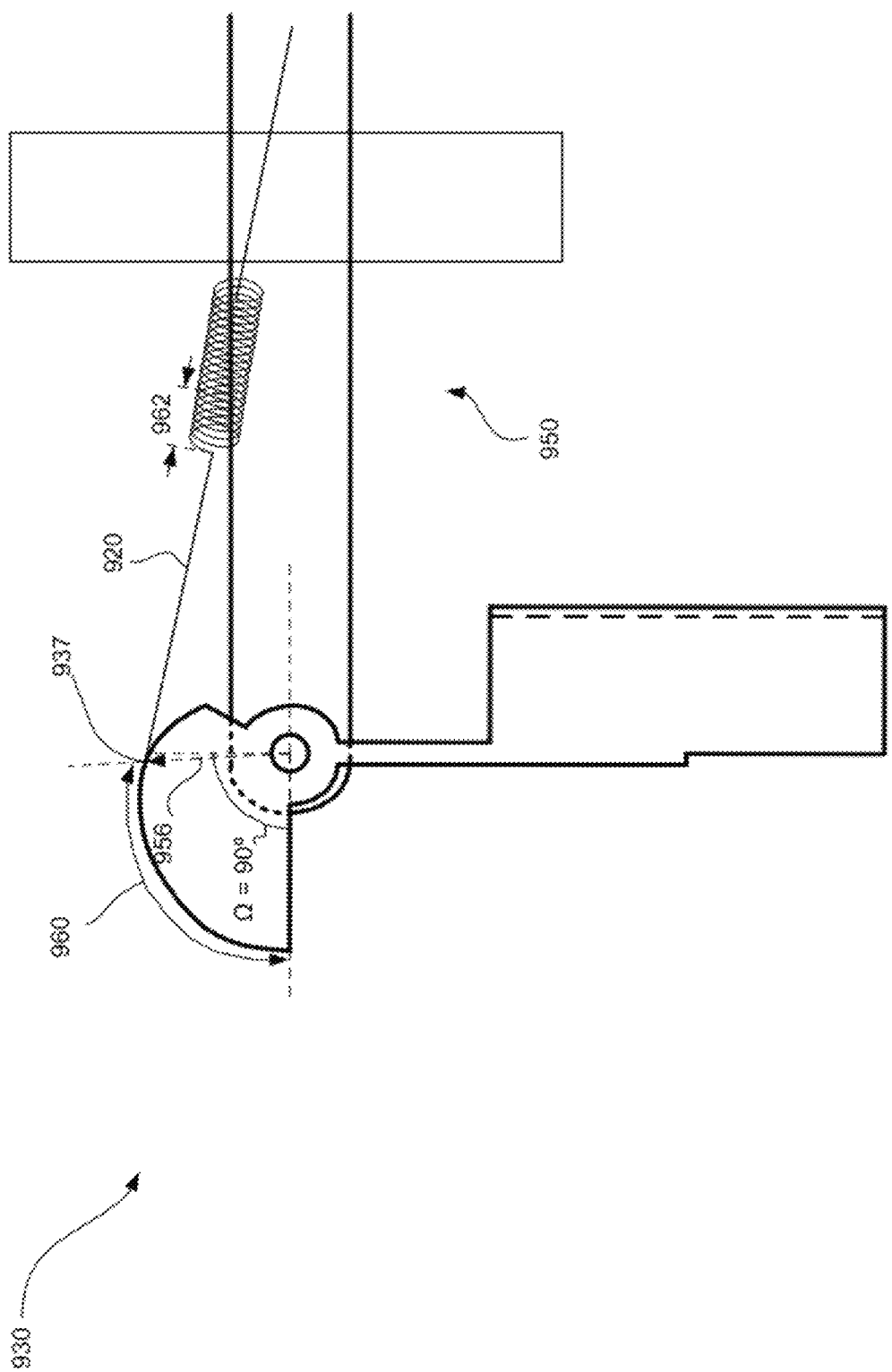
FIG. 9 illustrates a PCL brace shank portion coupled to a PCL brace thigh portion for a knee at a 105° flexion angle ($\Omega$).

FIG. 9 illustrates a shank portion 930 coupled to a thigh portion 950 for a knee at a 90° flexion angle (Ω). At flexion angle of 90°, the spline radius 956 at the tangent point 937 is smaller than the spline radius 856 in FIG. 8. The portion of the spline circumference 960 around which the spring 920 has wrapped is increased compared to that in FIG. 8. The spring 920 also sees greater displacement 962 than in FIG. 8, and the tangent point 937 is in a different location than in FIG. 8.

Figure 10:
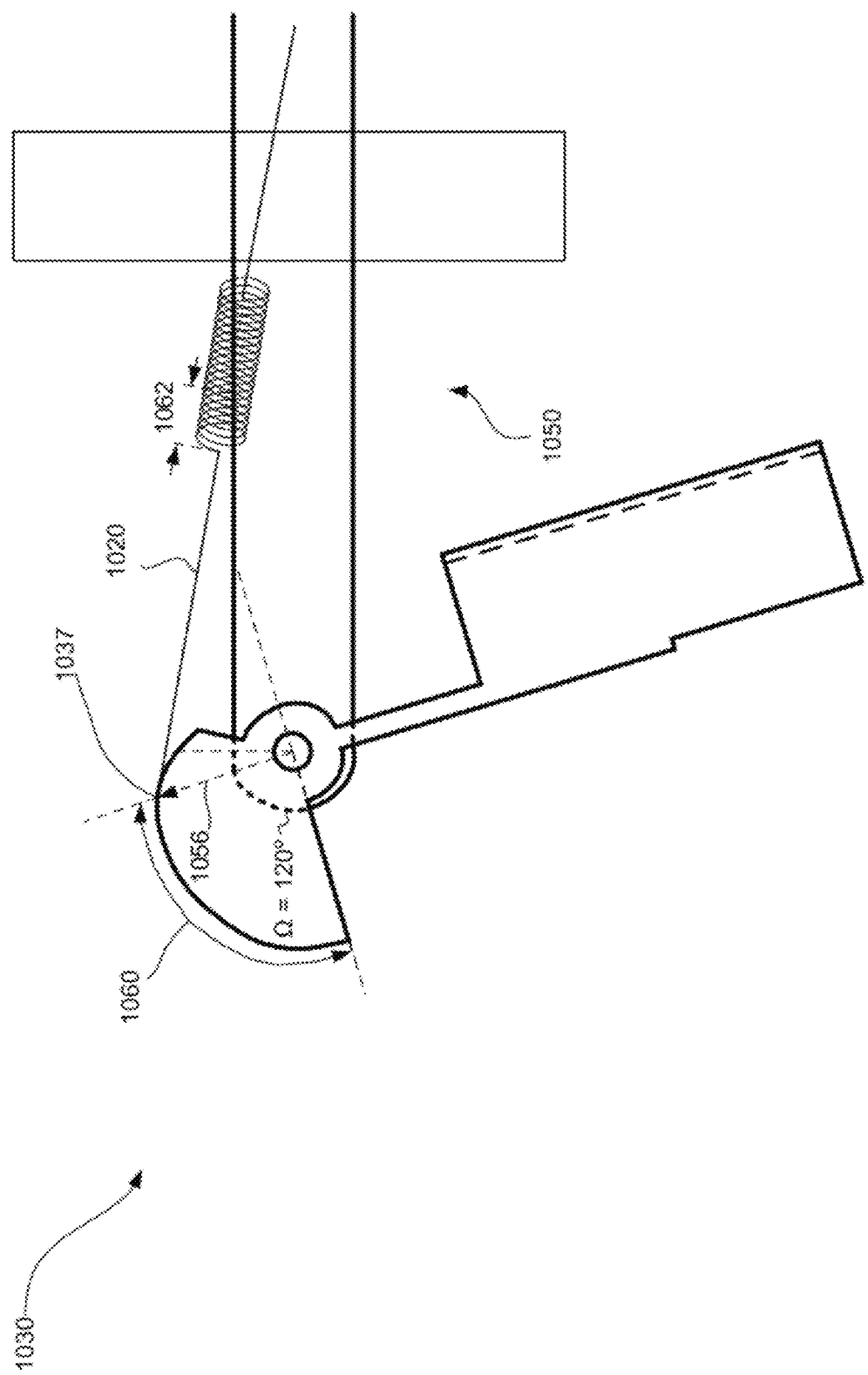
FIG. 10 illustrates a PCL brace shank portion coupled to a PCL brace thigh portion for a knee at a 120° flexion angle ($\Omega$).

FIG. 10 illustrates a shank portion 1030 coupled to a thigh portion 1050 for a knee at a 120° flexion angle (Ω). At flexion angle of 120°, the spline radius 1056 at the tangent point 1037 is smaller than the spline radius 956 in FIG. 9. The portion of the spline circumference 1060 around which the spring 1020 has wrapped is increased compared to that in FIG. 9. The spring 1020 also sees greater displacement 1062 than in FIG. 9, and the tangent point 1037 is in a different location than in FIG. 9.

Figure 13:
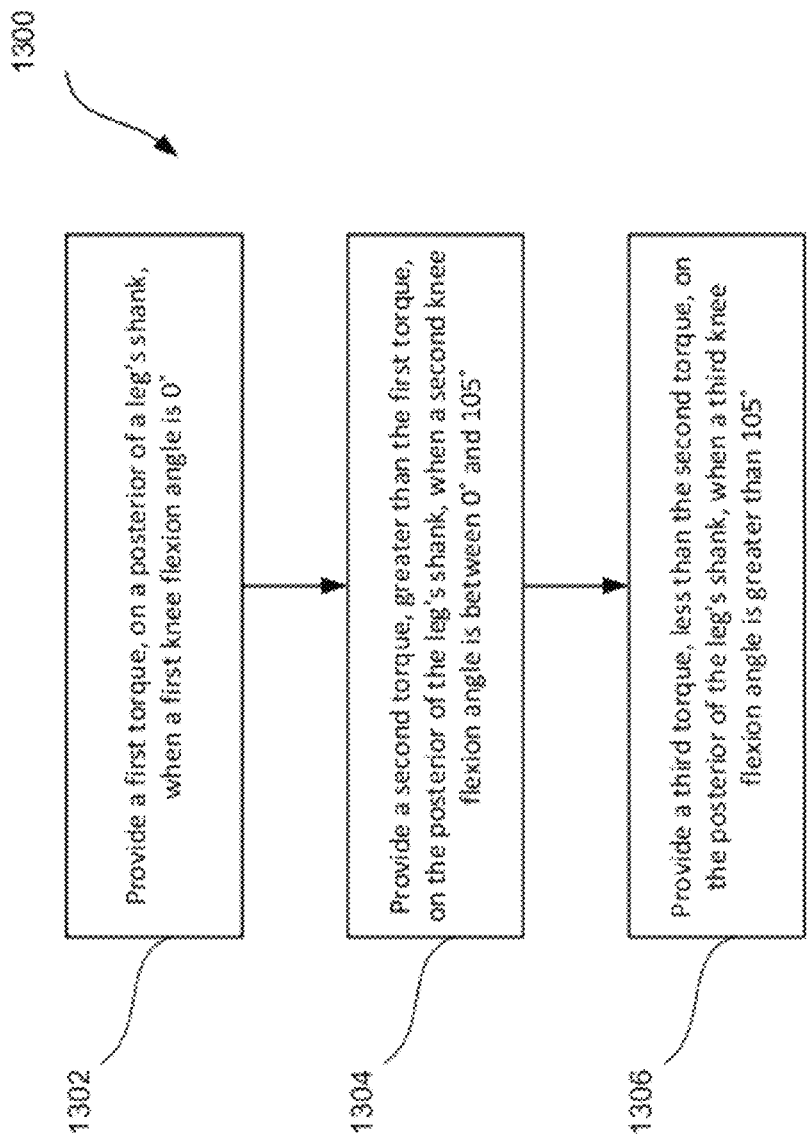
FIG. 13 illustrates one method carried out according to an embodiment of this disclosure.

FIG. 13 illustrates one method 1300 carried out according to an embodiment of this disclosure. The method 1300 can include providing a first torque, on a posterior of a leg's shank, when a first knee flexion angle is 0° in a first providing operation 1302. The method 1300 can further include providing a second torque, greater than the first torque, on the posterior of the leg's shank, when a second knee flexion angle is between 0° and 105° in a second providing operation 1304. The method 1300 can also include providing a third torque, less than the second torque, on the posterior of the leg's shank, when a third knee flexion angle is greater than 105° in a third providing operation 1306.

Figure 14:
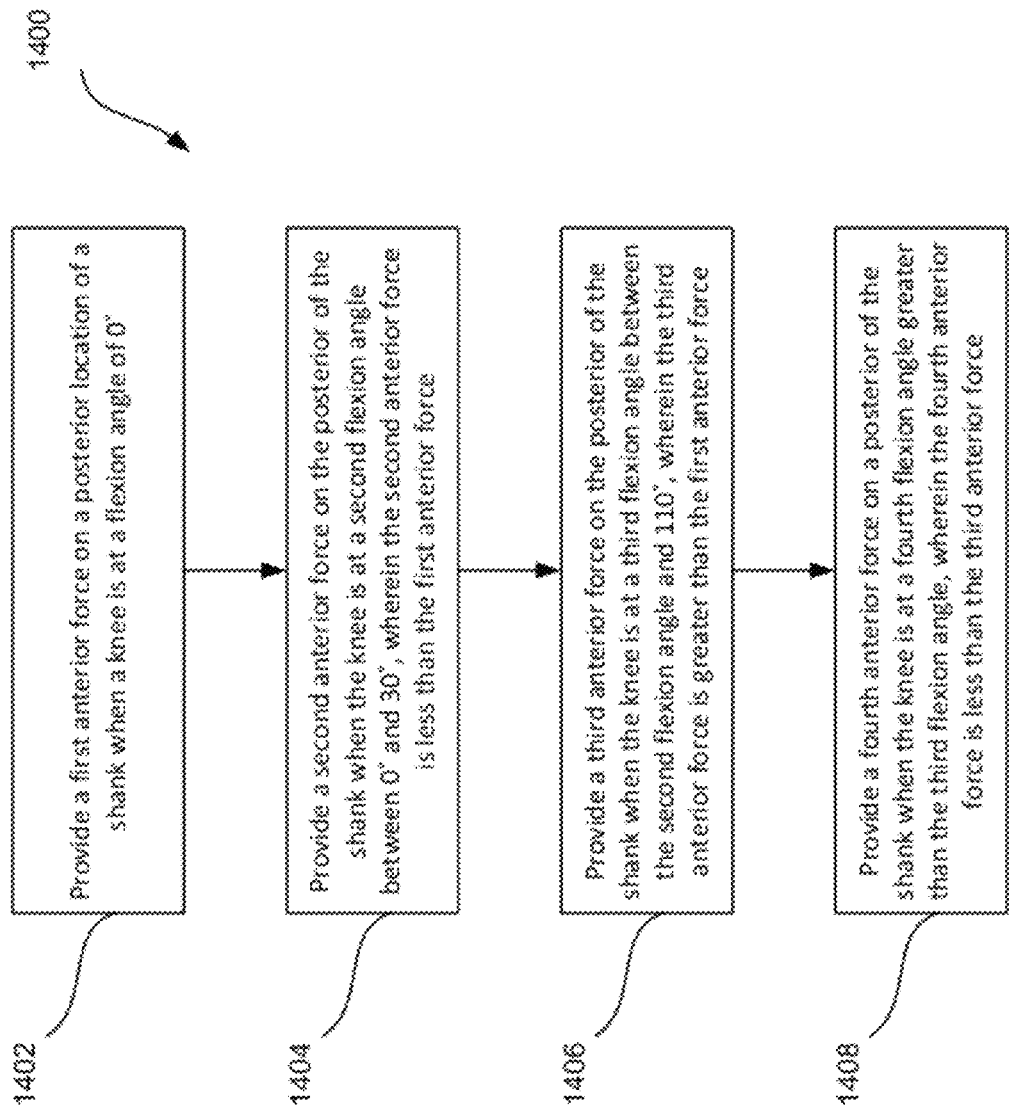
FIG. 14 illustrates another method carried out according to an embodiment of this disclosure.

FIG. 14 illustrates another method 1400 carried out according to an embodiment of this disclosure. The method 1400 may include providing a first anterior force on a posterior location of a shank when a knee is at a flexion angle of 0° in a first providing operation 1402. The method 1400 may further include providing a second anterior force on the posterior of the shank when the knee is at a second flexion angle between 0° and 30° in a second providing operation 1404. The second anterior force can be less than the first anterior force. Still further, the method 1400 may include providing a third anterior force on the posterior of the shank when the knee is at a third flexion angle between the second flexion angle and 110° in a third providing operation 1406. The third anterior force can be greater than the first anterior force. The method 1400 may also include providing a fourth anterior force on a posterior of the shank when the knee is at a fourth flexion angle greater than the third flexion angle in a fourth providing operation 1404. The fourth anterior force can be less than the third anterior force.

The present invention provides, among other things, a method, system, and apparatus for a knee brace providing a variable resistance force to replicate the forces provided by a healthy PCL. Those skilled in the art can readily recognize that numerous variations and substitutions may be made in the invention, its use, and its configuration to achieve substantially the same results as achieved by the embodiments described herein. Accordingly, there is no intention to limit the invention to the disclosed exemplary forms. Many variations, modifications, and alternative constructions fall within the scope and spirit of the disclosed invention.

What is claimed is:

1. An apparatus for bracing a knee, comprising:
a first portion configured to engage with an upper leg above a knee;
a second portion configured to engage with a lower leg below the knee;
a coupling element couping the first portion to the second portion such that the second portion can rotate about an axis at a pivot point and rotate relative to the first portion as a flexion angle changes, wherein the coupling element itself resists flexion with an anterior force on the posterior of the lower leg, wherein the anterior force is non-linearly related to the flexion angle;
wherein the coupling element includes a first spline located on a first side of the second portion, and a spring connecting to a second spring attachment site on the first spline located anterior of the pivot point and to a first spring attachment site near a center of gravity or center of torque on the first portion such that the forces exerted by the spring on the thigh portion cause less torque on the thigh portion;
wherein the first spline defines a variable radius such that a maximum radius is defined between the pivot point and the second spring attachment site.

2. The apparatus of claim 1, wherein the anterior force increases as a function of flexion angle below a first angular threshold, and the anterior force decreases as a function of flexion angle above the first angular threshold.

3. The apparatus of claim 2, wherein the anterior force decreases as a function of flexion angle below a second angular threshold, where the second angular threshold is less than the first angular threshold.

4. The apparatus of claim 3, wherein the first angular threshold is between 100° and 110°.

5. The apparatus of claim 4, wherein the first angular threshold is approximately between 90° and 105°.

6. The apparatus of claim 3, wherein the second angular threshold is between 0° and 10°.

7. The apparatus of claim 6, wherein the second angular threshold is approximately 5°.

8. The apparatus of claim 1, wherein the relation of the anterior force to the flexion angle is based on measured forces in one or more reference posterior cruciate ligaments.

9. The apparatus of claim 8, wherein the relation of the anterior force to the flexion angle is within a range of plus or minus 30 Newtons the measured forces in the one or more reference posterior cruciate ligaments.

10. The apparatus of claim 9, wherein the relation of the anterior force to the flexion angle is within a range of plus or minus 15 Newtons the measured forces in the one or more reference posterior cruciate ligaments.

11. The apparatus of claim 1, wherein the relation of the anterior force to the flexion angle is described by a polynomial equation.

12. The apparatus of claim 11, wherein the polynomial equation takes the form of:

$$Y = \epsilon(-0.00017x^3 + 0.0236x^2 + 0.0397x + 13.1)$$

where Y is the anterior force on the shank in Newtons;
x is the flexion angle in degrees; and
$\epsilon$ is an adjustable force multiplier.

13. The apparatus of claim 1, wherein the axis is static relative to the thigh portion.

14. An apparatus for bracing a knee, comprising:
a first portion configured to engage with a first region of a leg;

a second portion configured to engage with a second region of the leg;

a coupling element coupling the first portion to the second portion such that the second portion can rotate about an axis at a pivot point and rotate relative to the first portion as a flexion angle changes, wherein the coupling element itself resists flexion with an anterior force on the posterior of the second region of the leg, wherein the anterior force is nonlinearly related to the flexion angle;

wherein the coupling element includes a first spline located on a first side of the second portion, and a spring connecting to a first spring attachment of the first portion and to a second spring attachment site on the first spline , the spring is arranged along a variable tangent point according to rotation of the first spline and located along a periphery of the first spline.

15. The apparatus of claim 14, wherein an angle is defined along a first reference plane intersecting both the second spring attachment site and the pivot, such that a radius of the first spline decreases as the angle increases, an instantaneous point on the first spline where the spring is tangent to the first spline becomes ever closer to the pivot point as the first portion articulates relative to the second portion.

16. The apparatus of claim 15, wherein as the radius of the first spline decreases as the angle increases, as the first portion articulates relative to the second portion, the anterior force increases in a non-linear fashion.

17. The apparatus of claim 15, wherein beyond a threshold angle, the anterior force decreases as a result of a variable radius of the first spline.

18. The apparatus of claim 14, wherein the first spline defines a variable radius such that a maximum radius is defined between the pivot point and the second spring attachment site.

19. An apparatus for bracing a knee, comprising:

a first portion configured to engage with a first region of a leg;

a second portion configured to engage with a second region of the leg;

a coupling element coupling the first portion to the second portion such that the second portion can rotate about an axis at a pivot point and rotate relative to the first portion as a flexion angle changes, wherein the coupling element itself resists flexion with an anterior force on the posterior of the second region of the leg;

wherein the coupling element includes a first spline located on a first side of the second portion, and a spring connecting to a first spring attachment of the first portion and to a second spring attachment site on the first spline located anterior of the pivot point, the spring is arranged along a variable tangent point over a periphery of the first spline, wherein the first spline defines a variable radius such that a maximum radius is defined between the pivot point and the second spring attachment site and the radius of the first spline decreases as the first spline rotates from the maximum radius such that the anterior force increases in a non-linear fashion from the maximum radius as the first spline rotates.

* * * * *